United States Patent
Kai et al.

(10) Patent No.: US 9,614,166 B2
(45) Date of Patent: Apr. 4, 2017

(54) ORGANIC ELECTROLUMINESCENT ELEMENT

(71) Applicant: NIPPON STEEL & SUMIKIN CHEMICAL CO., LTD., Tokyo (JP)

(72) Inventors: Takahiro Kai, Kitakyushu (JP); Hideki Tanaka, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 256 days.

(21) Appl. No.: 14/414,406

(22) PCT Filed: Jul. 11, 2013

(86) PCT No.: PCT/JP2013/069005
§ 371 (c)(1),
(2) Date: Jan. 12, 2015

(87) PCT Pub. No.: WO2014/013936
PCT Pub. Date: Jan. 23, 2014

(65) Prior Publication Data
US 2015/0214495 A1    Jul. 30, 2015

(30) Foreign Application Priority Data
Jul. 19, 2012    (JP) .................. 2012-160344

(51) Int. Cl.
H01L 51/50    (2006.01)
H01L 51/00    (2006.01)
(Continued)

(52) U.S. Cl.
CPC ........ *H01L 51/0094* (2013.01); *C07D 405/14* (2013.01); *C07D 409/14* (2013.01);
(Continued)

(58) Field of Classification Search
None
See application file for complete search history.

(56) References Cited

U.S. PATENT DOCUMENTS

2002/0034655 A1    3/2002    Watanabe et al.
2006/0054861 A1    3/2006    Ionkin et al.
(Continued)

FOREIGN PATENT DOCUMENTS

JP    2009-267255 A    11/2009
JP    2009-267257       11/2009
(Continued)

OTHER PUBLICATIONS

Supplementary European Search Report for the Application No. EP 13 82 0636 dated—Nov. 23, 2015.
(Continued)

*Primary Examiner* — Gregory Clark
(74) *Attorney, Agent, or Firm* — Cheng Law Group, PLLC

(57) ABSTRACT

Provided is an organic electroluminescent device (organic EL device) that is improved in luminous efficiency, sufficiently secures driving stability, and has a simple construction. The organic electroluminescent device includes, between an anode and cathode laminated on a substrate, a plurality of organic layers. At least one layer of the organic layers contains a carbazole compound represented by the following general formula (1) having two to three structures in each of which a carbazole ring and a dibenzofuran or dibenzothiophene ring are bonded to each other at 1- and 4-positions. In the formula (1), A represents an n-valent aromatic hydrocarbon group or aromatic heterocyclic group, n represents an integer of 2 or 3, and X represents oxygen or sulfur.

4 Claims, 1 Drawing Sheet

(51) Int. Cl.
*C07D 405/14* (2006.01)
*C07D 409/14* (2006.01)
*H05B 33/20* (2006.01)
*C09K 11/06* (2006.01)
*H01L 51/52* (2006.01)

(52) U.S. Cl.
CPC ........ *H01L 51/006* (2013.01); *H01L 51/0061* (2013.01); *H01L 51/0073* (2013.01); *H01L 51/0074* (2013.01); *H01L 51/0081* (2013.01); *H01L 51/0085* (2013.01); *H01L 51/0091* (2013.01); *H05B 33/20* (2013.01); *C09K 11/06* (2013.01); *C09K 2211/1007* (2013.01); *C09K 2211/1029* (2013.01); *C09K 2211/1044* (2013.01); *C09K 2211/1088* (2013.01); *C09K 2211/1092* (2013.01); *C09K 2211/188* (2013.01); *H01L 51/0058* (2013.01); *H01L 51/0067* (2013.01); *H01L 51/0069* (2013.01); *H01L 51/0072* (2013.01); *H01L 51/5012* (2013.01); *H01L 51/5016* (2013.01); *H01L 51/5056* (2013.01); *H01L 51/5072* (2013.01); *H01L 51/5096* (2013.01); *H01L 51/5206* (2013.01); *H01L 51/5221* (2013.01); *H01L 2251/301* (2013.01)

(56) References Cited

U.S. PATENT DOCUMENTS

2009/0167165 A1* 7/2009 Otsu .................. C07D 209/86
 313/504
2009/0302745 A1 12/2009 Otsu et al.
2012/0104370 A1 5/2012 Suzuki et al.

FOREIGN PATENT DOCUMENTS

| JP | 2012-49518 A | 3/2012 |
| JP | 2012-124360 A | 6/2012 |
| WO | WO-01/41512 A1 | 6/2001 |
| WO | WO-2011/019156 A1 | 2/2011 |

OTHER PUBLICATIONS

International Search Report for the Application No. PCT/JP2013/069005 mailed Aug. 6, 2013.
English Translation of Written Opinion of the International Searching Authority (PCT/ISA/237) for Application No. PCT/JP2013/069005 dated Jan. 20, 2015.

* cited by examiner

ORGANIC ELECTROLUMINESCENT ELEMENT

TECHNICAL FIELD

The present invention relates to an organic electroluminescent device using an organic electroluminescent device material formed of a carbazole compound having a specific structure, and specifically, to a thin-film-type device that emits light when an electric field is applied to a light-emitting layer formed of an organic compound.

BACKGROUND ART

In general, an organic electroluminescent device (hereinafter referred to as organic EL device) is constructed of a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine and a light-emitting layer formed of a tris(8-hydroxyquinoline)aluminum complex (hereinafter referred to as Alq3) are formed between electrodes as thin films, resulting in a significant improvement in luminous efficiency, as compared to related-art devices in which a single crystal of anthracene or the like is used. Thus, the development of the above-mentioned organic EL device has been promoted in order to accomplish its practical application to a high-performance flat panel having features such as self-luminescence and rapid response.

Further, studies have been made on using phosphorescent light rather than fluorescent light as an attempt to raise the luminous efficiency of a device. Many kinds of devices including the above-mentioned device in which a hole-transporting layer formed of an aromatic diamine and a light-emitting layer formed of Alq3 are formed emit light by using fluorescent light emission. However, by using phosphorescent light emission, that is, by using light emission from a triplet excited state, luminous efficiency is expected to be improved by from about three times to four times, as compared to the case of using related-art devices in which fluorescent light (singlet) is used. In order to accomplish this purpose, studies have been made on adopting a coumarin derivative or a benzophenone derivative as a light-emitting layer, but extremely low luminance has only been provided. Further, studies have been made on using a europium complex as an attempt to use a triplet excited state, but highly efficient light emission has not been accomplished. In recent years, many studies centered on an organic metal complex such as an iridium complex have been made, as described in Patent Literature 1, for the purpose of attaining the high efficiency and long lifetime of light emission.

CITATION LIST

Patent Literature

[PTL 1] WO 01/041512 A1
[PTL 2] JP 2001-313178 A
[PTL 3] US 2006/0054861 A1
[PTL 4] JP 2009-267257 A
[PTL 5] JP 2009-267255 A
[PTL 6] WO 2007/119816 A1
[PTL 7] JP 2012-49518 A

In order to obtain high luminous efficiency, host materials that are used with the dopant materials described above play an important role. A typical example of the host materials proposed is 4,4'-di(9-carbazolyl)biphenyl (CBP) as a carbazole compound introduced in Patent Literature 2. When CBP is used as a host material for a green phosphorescent light-emitting material typified by a tris(2-phenylpyridine) iridium complex (Ir(ppy)3), the charge injection/transportation balance is disturbed because CBP has the characteristic of facilitating the delivery of holes and not facilitating the delivery of electrons. Thus, excessively delivered holes flow out into an electron-transporting layer side, with the result that the luminous efficiency from Ir(ppy)3 lowers.

As described above, in order to provide high luminous efficiency to an organic EL device, it is necessary to use a host material that has high triplet excitation energy, and is striking a good balance in both charge (hole and electron)-injecting/transporting property. Further desired is a compound that has electrochemical stability, has high heat resistance, and has excellent amorphous stability, and hence further improvement has been demanded.

Patent Literature 3 discloses the carbazole compound as shown below as the host material for the organic EL device.

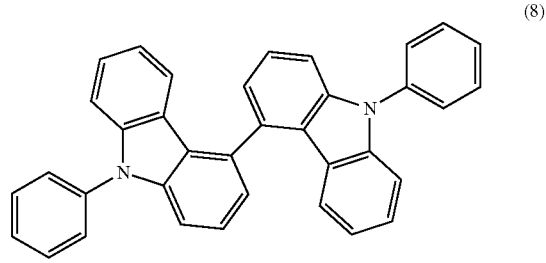 [SMILES: c1ccc(-n2c3ccccc3c3c(-c4cccc5c4c4ccccc4n5-c4ccccc4)cccc32)cc1]

(8)

However, Patent Literature 3 merely discloses, for example, a biscarbazole compound having a skeleton in which the 4-position of a carbazole molecule and the 4-position of another carbazole molecule are bonded to each other.

Patent Literature 4 discloses the carbazole compound as shown below as the host material for the organic EL device.

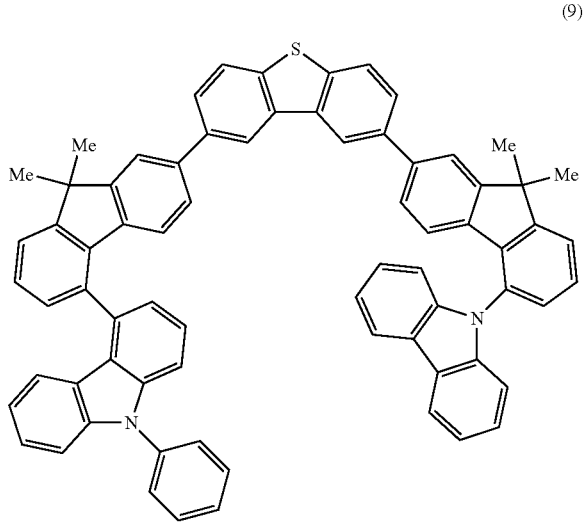 [SMILES: CC1(C)c2cc(-c3ccc4sc5ccc(-c6ccc7c(c6)C(C)(C)c6cccc(-n8c9ccccc9c9ccccc98)c6-7)cc5c4c3)ccc2-c2c(-c3cccc4c3c3ccccc3n4-c3ccccc3)cccc21]

(9)

However, Patent Literature 4 merely discloses, for example, a compound having a skeleton in which the 4-position of carbazole and the 4-position of fluorene are bonded to each other.

Patent Literatures 5, 6, and 7 disclose the carbazole compound as shown below as the host material for the organic EL device.

(10)

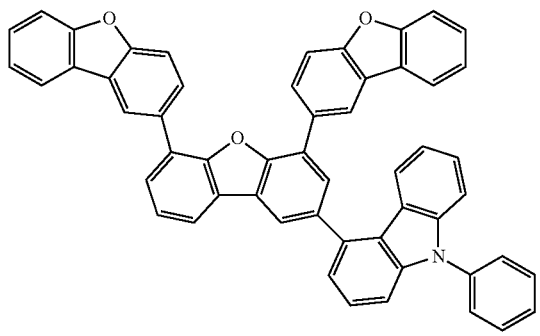

(11)

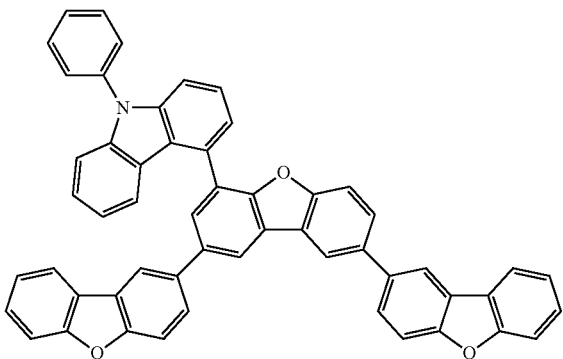

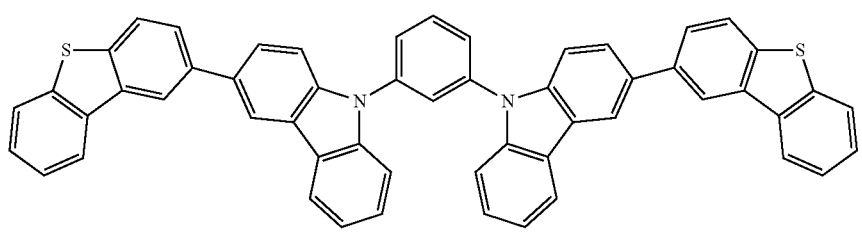

(12)

(13)

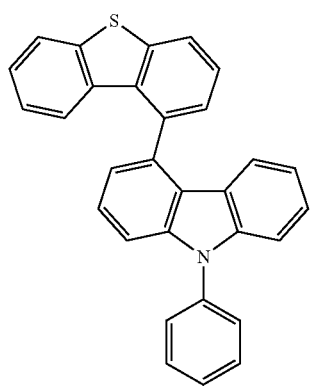

(14)

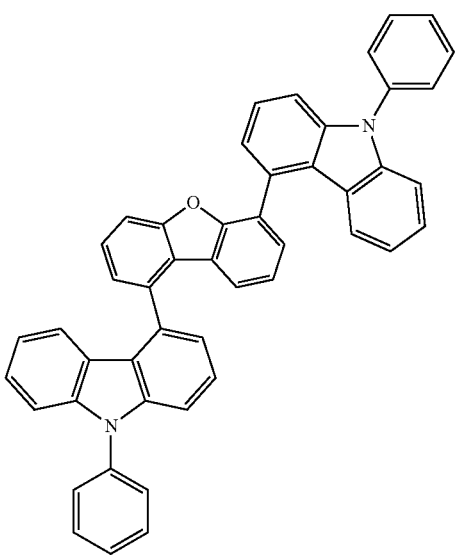

However, none of those literatures discloses the usefulness of an organic EL device using a compound having, in the same molecule thereof, two or more skeletons in each of which the 4-position of carbazole and the 1-position of dibenzofuran or dibenzothiophene are bonded to each other.

SUMMARY OF INVENTION

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, an organic EL device that has high efficiency, has high driving stability, and is practically useful and a compound suitable for the organic EL device.

The inventors of the present invention have made extensive studies, and as a result, have found that when a compound having, in the same molecule thereof, two or more skeletons in each of which the 4-position of carbazole and the 1-position of dibenzofuran or dibenzothiophene are bonded to each other is used in an organic EL device, the device shows excellent characteristics. Thus, the inventors have completed the present invention.

The present invention relates to an organic electroluminescent device, having a structure in which an anode, an organic layer, and a cathode are laminated on a substrate, in which at least one layer selected from the group consisting of a light-emitting layer, a hole-transporting layer, an electron-transporting layer, a hole-blocking layer, an electron-blocking layer, and an exciton-blocking layer contains a carbazole compound represented by the general formula (1).

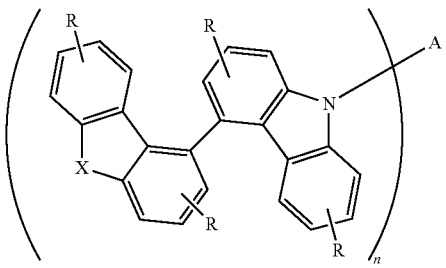

(1)

In the formula, A represents an n-valent aromatic hydrocarbon group having 6 to 30 carbon atoms, an n-valent aromatic heterocyclic group having 3 to 30 carbon atoms, or an n-valent aromatic group in which two to six of the aromatic hydrocarbon groups and the aromatic heterocyclic groups are linked to each other, and n represents an integer of 2 or 3. When the aromatic hydrocarbon group or the aromatic heterocyclic group has substituents, the substituents each independently represent an alkyl group having 1 to 10 carbon atoms, a cycloalkyl group having 3 to 10 carbon atoms, an alkoxy group having 1 to 10 carbon atoms, —OAr, —N(Ar)$_2$, or —Si(Ar)$_3$. R's each independently represent hydrogen, an alkyl group having 1 to 10 carbon atoms, a cycloalkyl group having 3 to 10 carbon atoms, an alkoxy group having 1 to 10 carbon atoms, —OAr, —N(Ar)$_2$, —Si(Ar)$_3$, an aromatic hydrocarbon group having 6 to 10 carbon atoms, an aromatic heterocyclic group having 3 to 10 carbon atoms, or an aromatic group in which two to three of the aromatic hydrocarbon groups and the aromatic heterocyclic groups are linked to each other. Ar's each represent an aromatic hydrocarbon group having 6 to 10 carbon atoms, an aromatic heterocyclic group having 3 to 10 carbon atoms, or an aromatic group in which two to three of the aromatic hydrocarbon groups and the aromatic heterocyclic groups are linked to each other, and the plurality of Ar's may be identical to or different from each other. X's each independently represent oxygen or sulfur. In addition, the aromatic hydrocarbon group and the aromatic heterocyclic group may each have a substituent.

In the general formula (1), it is preferred that R's each represent hydrogen. In addition, in the general formula (1), A may represent an n-valent aromatic group represented by any one of the following formulae (2) to (5).

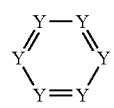

(2)

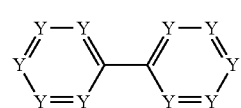

(3)

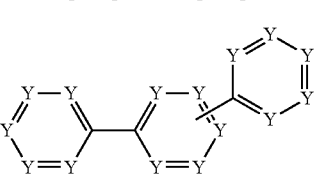

(4)

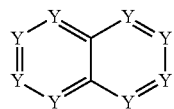

(5)

In the formulae (2) to (5): Y's each independently represent C, C(R), or nitrogen, and n Y's each represent C, provided that n+1 Y's in the formula (4) each represent carbon (C). n and R each have the same meaning as that in the general formula (1). n C's have bonding sites for providing an n-valent group. Further, one of Y's present in the central ring in the formula (4) has C bonded to an adjacent ring.

The layer containing the carbazole compound represented by the general formula (1) may include a light-emitting layer containing a phosphorescent light-emitting dopant.

ADVANTAGEOUS EFFECTS OF INVENTION

The carbazole compound represented by the general formula (1) to be used in the organic EL device of the present invention has, in the same molecule thereof, two or more skeletons in each of which the 4-position of carbazole and the 1-position of dibenzofuran or dibenzothiophene are bonded to each other. Accordingly, as compared to the case where carbazole and dibenzofuran or dibenzothiophene are bonded to each other at other substitution positions or the case where the substitution positions are the same as those described above but the compound has only one skeleton of such kind in the same molecule thereof, electron-transporting property can be improved while additionally high hole-transporting property is maintained. Further, the carbazole compound has balanced and excellent injecting/transporting characteristics for both charges. Accordingly, when the compound is used as a phosphorescent host material in the organic EL device, a balance between the charges in its light-emitting layer becomes good. Probably as a result of the foregoing, the probability that a hole and an electron recombine with each other increases, and hence the organic EL device of the present invention achieves high luminous efficiency.

When the carbazole compound is used as a material for the hole-transporting layer or the electron-blocking layer, the compound reduces the driving voltage of the device and improves the luminous efficiency thereof because of its good hole-injecting/transporting characteristics.

In addition, the carbazole compound has the energy of the lowest triplet excited state high enough to confine the energy of the lowest triplet excited state of a dopant. Accordingly, when the compound is used as a material for the exciton-blocking layer, the transfer of triplet excitation energy from the dopant to the adjacent layer containing the compound can be effectively suppressed, and hence high luminous efficiency can be obtained.

In addition, the carbazole compound has, in the same molecule thereof, the two or more skeletons in each of which the 4-position of carbazole and the 1-position of dibenzofuran or dibenzothiophene are bonded to each other. Accordingly, as compared to the case where the compound has only one skeleton of such kind in the same molecule thereof, the compound has a high glass transition point, shows additionally high heat stability and a good amorphous characteristic, and is electrochemically stable. Accordingly, an organic EL device having a long driving lifetime and high durability can be realized.

The organic EL device according to the present invention has practically satisfactory levels of light-emitting characteristic, driving lifetime, and durability, and its technical value is high in its application to, for example, flat panel displays (such as a cellular phone display device, an on-vehicle display device, an OA computer display device, and a television), light sources each taking advantage of the feature of the device as a surface emitter (lighting, a light source for a copying machine, and backlight sources for a liquid crystal display and meters), display boards, and identification lamps.

DESCRIPTION OF EMBODIMENTS

Figure 1:
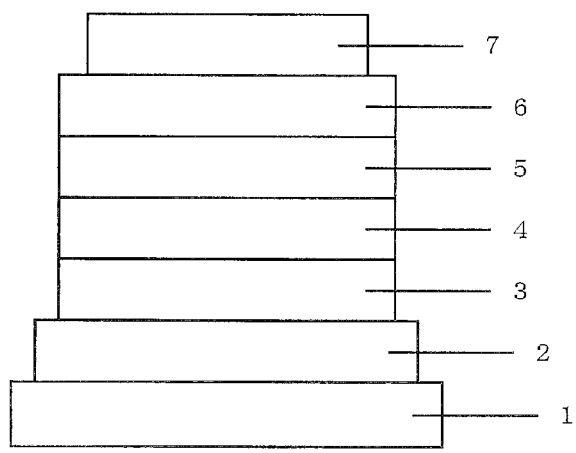
FIG. 1 is a sectional view illustrating an example of the structure of an organic EL device.

An organic EL device of the present invention contains a carbazole compound represented by the general formula (1) in an organic layer thereof.

In the general formula (1), A represents an n-valent aromatic hydrocarbon group having 6 to 30 carbon atoms, an n-valent aromatic heterocyclic group having 3 to 30 carbon atoms, or an n-valent aromatic group in which two to six of the aromatic hydrocarbon groups and the aromatic heterocyclic groups are linked to each other. A preferably represents an aromatic hydrocarbon group having 6 to 10 carbon atoms, an aromatic heterocyclic group having 3 to 10 carbon atoms, or an aromatic group in which two to six of the aromatic hydrocarbon groups and the aromatic heterocyclic groups are linked to each other. In the case of the aromatic heterocyclic group, a hetero atom constituting its aromatic heterocycle is preferably, for example, oxygen, sulfur, nitrogen, or silicon, more preferably nitrogen. The number of the hetero atoms is preferably from 1 to 3. Although the aromatic hydrocarbon group and the aromatic heterocyclic group may each be a monocycle or may each be a fused ring, the groups are each preferably a monocycle or a fused ring having 2 to 3 rings, more preferably a monocycle or a fused ring having 2 rings. n represents an integer of 2 or 3.

The aromatic hydrocarbon group or the aromatic heterocyclic group may be an unsubstituted aromatic hydrocarbon group or aromatic heterocyclic group, or may be a substituted aromatic hydrocarbon group or aromatic heterocyclic group. In the case of the aromatic group in which aromatic hydrocarbon groups or aromatic heterocyclic groups are linked to each other, the aromatic hydrocarbon groups or aromatic heterocyclic groups in the aromatic group may be identical to or different from each other, and the aromatic group may contain both an aromatic hydrocarbon group and an aromatic heterocyclic group.

Specific examples of the unsubstituted aromatic hydrocarbon group or aromatic heterocyclic group include n-valent groups each produced by removing n hydrogen atoms from, for example, benzene, pentalene, indene, naphthalene, azulene, heptalene, octalene, indacene, acenaphthylene, fluorene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, hexahelicene, hexaphene, hexacene, rubicene, coronene, trinaphthylene, heptaphene, heptacene, pyranthrene, furan, pyran, thiophene, thiopyran, pyrrole, imidazole, pyrazole, oxazole, isooxazole, thiazole, isothiazole, selenazole, tellurazole, pyridine, pyrazine, pyrimidine, pyridazine, triazine, silole, benzofuran, isobenzofuran, isochromene, chromene, dibenzofuran, xanthene, oxanthrene, peri-xanthenoxanthene, thianaphthene, isothianaphthene, isothiochromene, thiochromene, thiophanthrene, dibenzothiophene, thioxanthene, thianthrene, phenoxathiin, indolizine, indole, isoindole, benzimidazole, indazole, purine, benzoxazole, benzisoxazole, benzothiazole, benzisothiazole, quinolizine, quinoline, isoquinoline, naphthyridine, phthalazine, quinoxaline, quinazoline, cinnoline, pteridine, carbazole, carboline, phenanthridine, acridine, perimidine, phenanthroline, phenazine, phenoxazine, phenothiazine, phenoselenazine, phenotellurazine, anthyridine, silaindene, silafluorene, silaanthracen, silanthrene, phenoxasilin, phenothiasilin, or phenazacillin. Preferred examples thereof include n-valent groups each produced by removing n hydrogen atoms from benzene, naphthalene, furan, thiophene, pyrrole, imidazole, pyrazole, oxazole, isooxazole, thiazole, isothiazole, pyridine, pyrazine, pyrimidine, pyridazine, triazine, silole, benzofuran, isobenzofuran, thianaphthene, isothianaphthene, indole, isoindole, benzimidazole, indazole, benzoxazole, benzisoxazole, benzothiazole, benzisothiazole, quinoline, isoquinoline, naphthyridine, phthalazine, quinoxaline, quinazoline, cinnoline, or silaindene.

In the case of an aromatic group in which a plurality of unsubstituted aromatic hydrocarbon groups or aromatic heterocyclic groups are linked to each other (hereinafter referred to as "linked aromatic group"), the aromatic hydrocarbon group or aromatic heterocyclic group described above is, or both thereof are, suitable for the unsubstituted aromatic hydrocarbon groups or aromatic heterocyclic groups constituting the linked aromatic group. In this case, in order that the entirety of the linked aromatic group may become an n-valent group, the valence of each of the unsubstituted aromatic hydrocarbon groups or aromatic heterocyclic groups constituting the linked aromatic group may be different from that described above. In addition, it is not desired that the linked aromatic group include a structure appearing in the general formula (1) in which a dibenzofuran ring or dibenzothiophene ring (both the rings are referred to as "DBFT rings") and a carbazole ring are directly bonded to each other.

The number of groups to be linked to each other in the linked aromatic group is preferably from 2 to 4, more preferably from 2 to 3, and the aromatic rings to be linked to each other may be identical to or different from each other. In that case, a bonding position to be bonded to nitrogen of carbazole in the formula (1) is not limited, and may be a ring in a terminal portion of the aromatic rings linked to each other or may be a ring in a central portion thereof. Here, the term "aromatic rings" is a generic term for the aromatic hydrocarbon group and the aromatic heterocyclic group.

Here, a divalent linked aromatic group produced from an aromatic compound in which 2 to 6 aromatic rings are linked to each other is represented by, for example, any one of the following formulae.

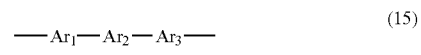
(15)

(16)

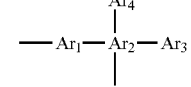

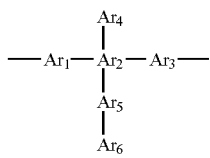

(17)

(In the formulae (15) to (17), $Ar_1$ to $Ar_6$ each represent a substituted or unsubstituted aromatic ring.)

In the case of the linked aromatic group, the group may be unsubstituted or may have a substituent. An n-valent unsubstituted linked aromatic group produced from an aromatic compound in which 2 to 6 aromatic rings are linked to each other is specifically exemplified by n-valent groups each produced by removing n hydrogen atoms from, for example, biphenyl, phenylpyridine, phenylpyrimidine, phenyltriazine, bipyridine, bipyrimidine, bitriazine, terphenyl, diphenylpyridine, diphenylpyrimidine, diphenyltriazine, bistriazinylbenzene, terpyridine, phenylterphenyl, phenylnaphthalene, phenylquinoline, binaphthalene, biquinoline, diphenylnaphthalene, diphenylquinoline, phenyldibenzofuran, phenyldibenzothiophene, phenylcarbazole, dibenzofuranylpyridine, dibenzothienylpyridine, pyridylcarbazole, dibenzofuranylcarbazole, dibenzothienylcarbazole, carbazolylcarbazole, diphenylcarbazole, carbazolylbiphenyl, carbazolylterphenyl, biscarbazolylbenzene, or biscarbazolylbiphenyl. Preferred examples thereof include an n-valent groups each produced by removing n hydrogen atoms from biphenyl, phenylpyridine, phenylpyrimidine, phenyltriazine, bipyridine, bipyrimidine, bitriazine, terphenyl, diphenylpyridine, diphenylpyrimidine, diphenyltriazine, bistriazinylbenzene, terpyridine, phenylnaphthalene, or phenylquinoline.

The aromatic hydrocarbon group or the aromatic heterocyclic group may have a substituent, and when any such group has a substituent, the total number of substituents is from 1 to 6, preferably from 1 to 4, more preferably from 1 to 2. In addition, when the aromatic hydrocarbon group or the aromatic heterocyclic group has 2 or more substituents, the substituents may be identical to or different from each other. When the linked aromatic group has a substituent, the substituent is the same as the substituent of anyone of the aromatic hydrocarbon groups or aromatic heterocyclic groups constituting the linked aromatic group.

When the aromatic hydrocarbon group or the aromatic heterocyclic group has substituents, the substituents are each independently an alkyl group having 1 to 10 carbon atoms, a cycloalkyl group having 3 to 10 carbon atoms, an alkoxy group having 1 to 10 carbon atoms, —OAr, —N(Ar)$_2$, or —Si(Ar)$_3$. Ar represents an aromatic hydrocarbon group having 6 to 10 carbon atoms, an aromatic heterocyclic group having 3 to 10 carbon atoms, or a linked aromatic group in which two to three of the aromatic hydrocarbon groups and the aromatic heterocyclic groups are linked to each other, and a plurality of Ar's may be identical to or different from each other. In addition, when Ar represents the aromatic hydrocarbon group, the aromatic heterocyclic group, or the linked aromatic group, any such group can have a substituent but the number of its carbon atoms is limited to the above-mentioned range. The substituent, which is selected from the foregoing, is preferably an alkyl group having 1 to 6 carbon atoms or an alkoxy group having 1 to 6 carbon atoms.

Specific examples of the alkyl group include a methyl group, an ethyl group, a propyl group, a butyl group, a pentyl group, a hexyl group, a heptyl group, an octyl group, a nonyl group, and a decyl group. Preferred examples thereof include a methyl group, an ethyl group, a propyl group, a butyl group, a pentyl group, a hexyl group, a heptyl group, and an octyl group. More preferred examples thereof include alkyl groups each having 1 to 6 carbon atoms, such as a methyl group, an ethyl group, a propyl group, a butyl group, a pentyl group, and a hexyl group. The alkyl group may be linear or branched.

Specific examples of the cycloalkyl group include a cyclopropyl group, a cyclobutyl group, a cyclopentyl group, a cyclohexyl group, a methylcyclohexyl group, a cycloheptyl group, a cyclooctyl group, a cyclononyl group, and a cyclodecyl group. Preferred examples thereof include cycloalkyl groups each having 3 to 8 carbon atoms, such as a cyclopentyl group, a cyclohexyl group, and a methylcyclohexyl group.

Specific examples of the alkoxy group include a methoxy group, an ethoxy group, a propoxy group, a butoxy group, a pentyloxy group, a hexyloxy group, a heptyloxy group, an octyloxy group, a nonyloxy group, and a decyloxy group. Preferred examples thereof include a methoxy group, an ethoxy group, a propoxy group, a butoxy group, a pentyloxy group, a hexyloxy group, a heptyloxy group, and an octyloxy group. More preferred examples thereof include alkoxy groups each having 1 to 6 carbon atoms, such as a methoxy group, an ethoxy group, a propoxy group, a butoxy group, a pentyloxy group, and a hexyloxy group. The alkoxy group may be linear or branched.

In the general formula (1), A represents, for example, preferably an n-valent group represented by any one of the formulae (2) to (5), more preferably an n-valent group represented by the formula (2), (3), or (4). In the formulae (2) to (5), Y's each independently represent C, C(R), or nitrogen, and n Y's each represent C, provided that n+1 Y's in the formula (4) each represent C. Of Y's constituting each six-membered ring, 0 to 3 Y's each preferably represent nitrogen. n C's providing an n-valent group may be present in the same ring or may be present in different rings. Here, n and R have the same meanings as those of n and R of the general formula (1).

In the general formula (1) and in the case where Y's each represent C(R), R's each independently represent hydrogen, an alkyl group having 1 to 10 carbon atoms, a cycloalkyl group having 3 to 10 carbon atoms, an alkoxy group having 1 to 10 carbon atoms, —OAr, —N(Ar)$_2$, —Si(Ar)$_3$, an aromatic hydrocarbon group having 6 to 10 carbon atoms, an aromatic heterocyclic group having 3 to 10 carbon atoms, or a linked aromatic group in which two to three of the aromatic hydrocarbon groups and the aromatic heterocyclic groups are linked to each other. R's each independently preferably represent hydrogen, an alkyl group having 1 to 6 carbon atoms, a cycloalkyl group having 3 to 8 carbon atoms, an alkoxy group having 1 to 6 carbon atoms, an aromatic hydrocarbon group having 6 to 10 carbon atoms, an aromatic heterocyclic group having 3 to 10 carbon atoms, or a linked aromatic group in which two to three of the aromatic hydrocarbon groups and the aromatic heterocyclic groups are linked to each other.

Here, Ar in —OAr, —N(Ar)$_2$, or —Si(Ar)$_3$ has the same meaning as that of Ar in —OAr, —N(Ar)$_2$, or —Si(Ar)$_3$ described as a substituent in the case where the aromatic hydrocarbon group or aromatic heterocyclic group in the description of A of the general formula (1) has the substituent. In addition, the aromatic hydrocarbon group, the aromatic heterocyclic group, or the linked aromatic group is the same as that represented by A of the general formula (1) except that the range of the number of carbon atoms is different. Specific examples of the alkyl group, the cycloalkyl group, or the alkoxy group are the same as those of any such group described as a substituent in the case where the aromatic hydrocarbon group or aromatic heterocyclic group in the description of A of the general formula (1) has the substituent.

In the general formula (1) and the formulae (2) to (5), symbols or formulae identical to each other are interpreted as having the same meaning unless otherwise stated.

In the general formula (1), X's each independently represent oxygen or sulfur.

The carbazole compound to be used in the organic EL device of the present invention can be synthesized by employing a known approach from a DBFT-carbazole compound using a carbazole derivative whose 4-position is substituted with a halogen atom and a dibenzofuran derivative or dibenzothiophene derivative whose 1-position is substituted with a halogen atom as starting raw materials, the compound having a skeleton in which the 4-position of carbazole and the 1-position of dibenzofuran or dibenzothiophene are bonded to each other, through the selection of raw materials in accordance with the structure of a target compound.

For example, a DBT-carbazole compound having a skeleton in which the 4-position of carbazole and the 1-position of dibenzothiophene (DBT) are bonded to each other can be synthesized by the Suzuki-Miyaura cross-coupling reaction with 4-bromocarbazole after the transformation of the bromine atom of 1-bromodibenzothiophene into a boronic acid pinacol ester with reference to a synthesis example described in The Journal of Organic Chemistry 1995, 60, 7508-7510.

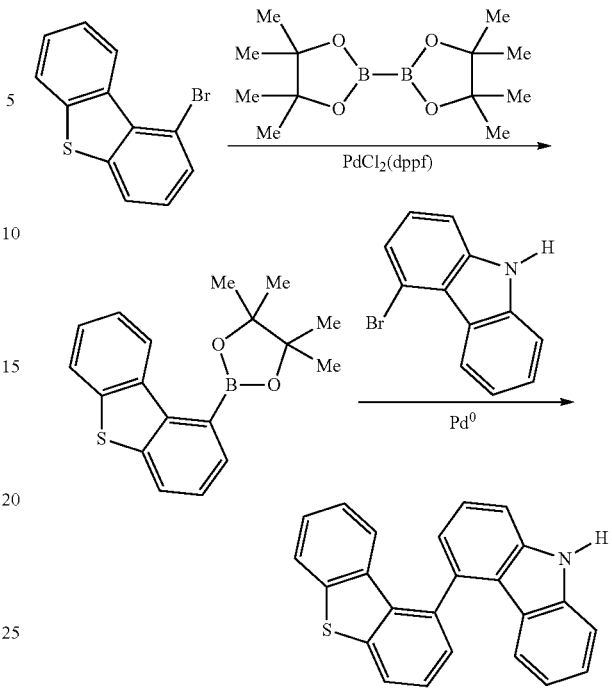

The carbazole compound represented by the general formula (1) can be synthesized by substituting the hydrogen atom on nitrogen of the DBT-carbazole compound with the corresponding aromatic group through a coupling reaction such as the Ullmann reaction.

Specific examples of the carbazole compound represented by the general formula (1) are shown below. However, the carbazole compound is not limited thereto.

(21)

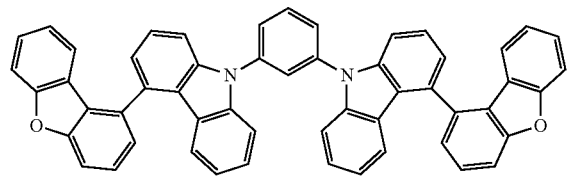

(22)

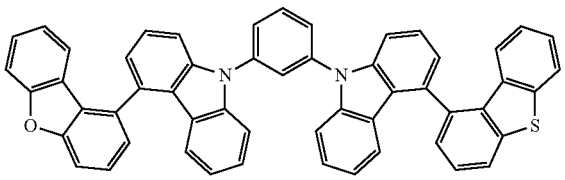

(23)

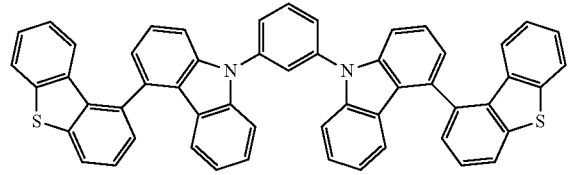

(24)

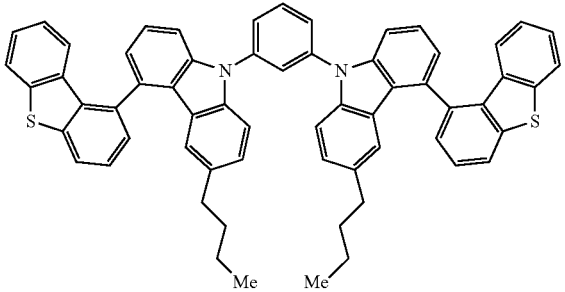

-continued
(25)
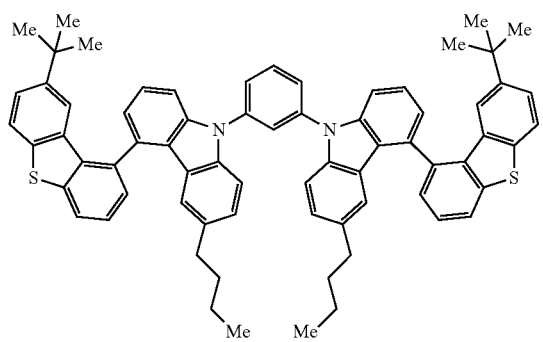
(26)
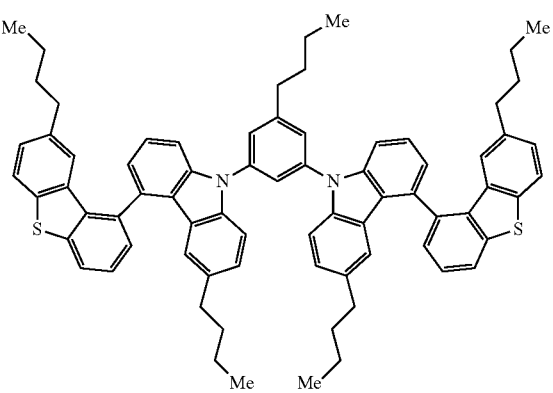
(27)
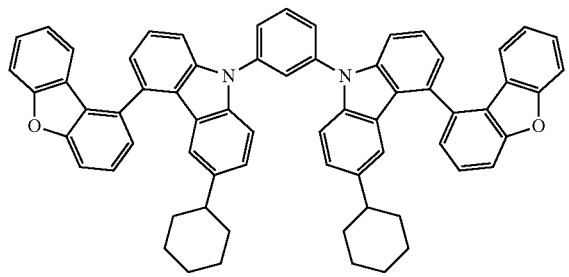
(28)
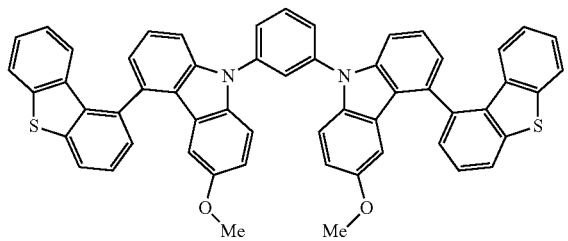
(29)
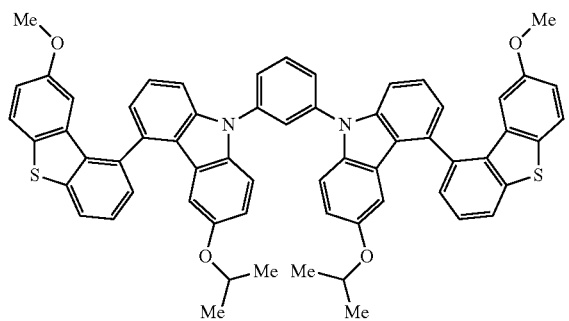
(30)
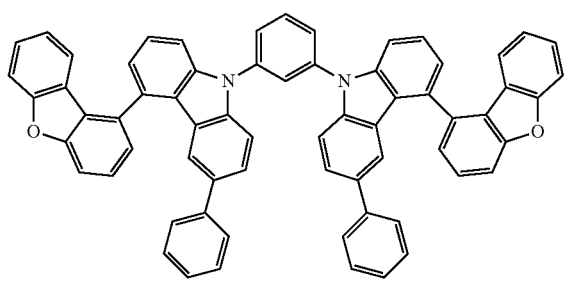
(31)
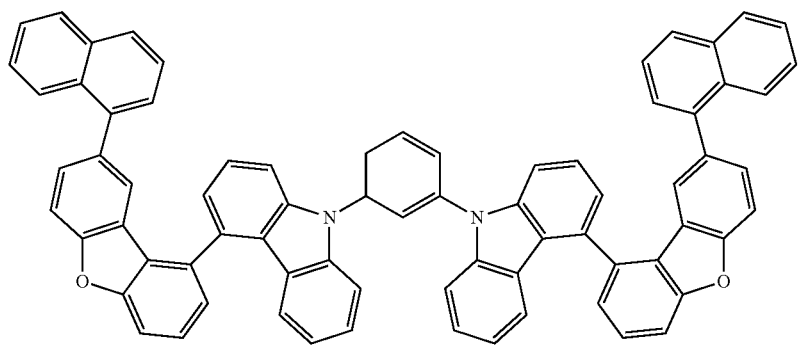

-continued
(36)
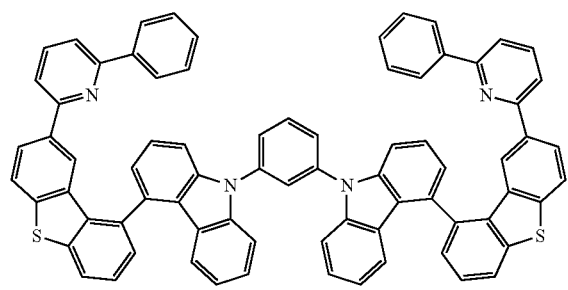
(38)
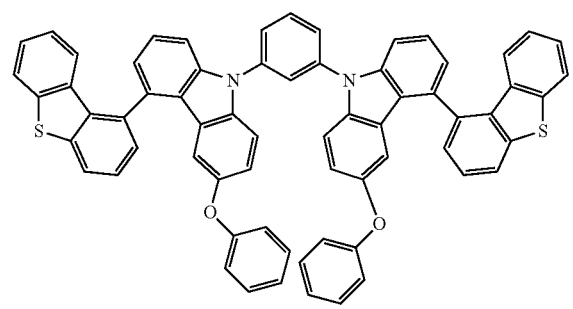
(39)
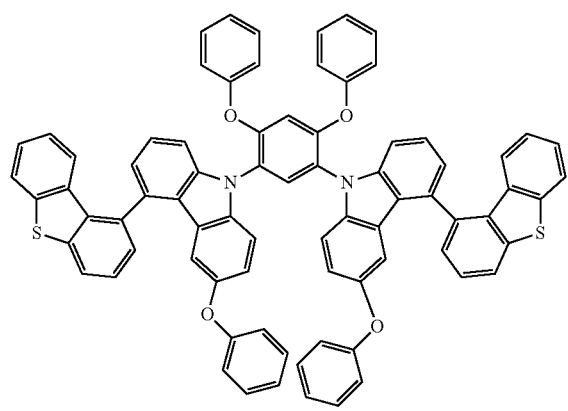
(40)
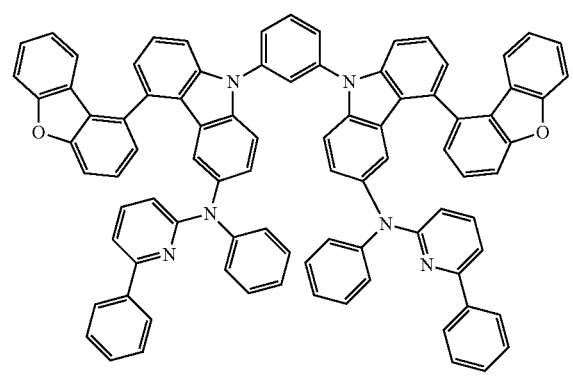
(41)
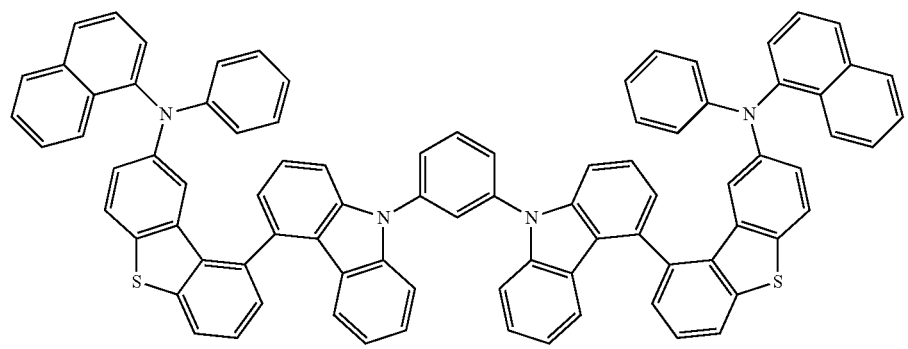
(42)
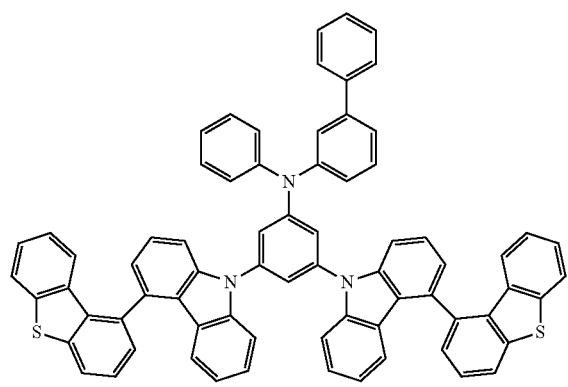
(44)
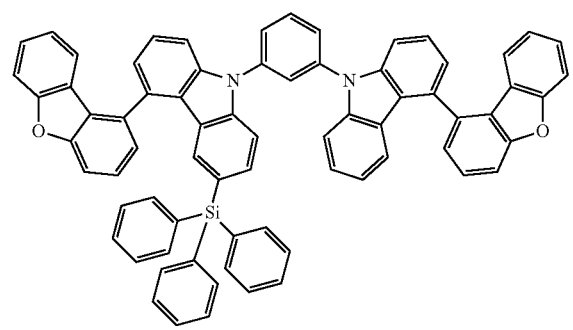

-continued
(45)
(46)
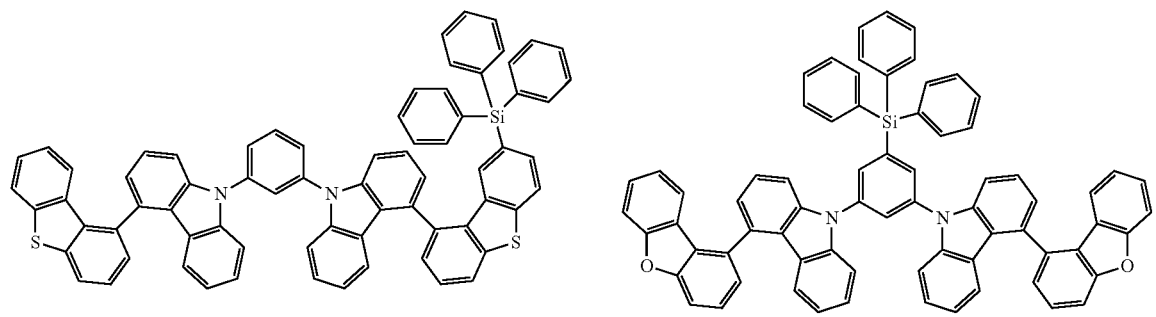
(47)
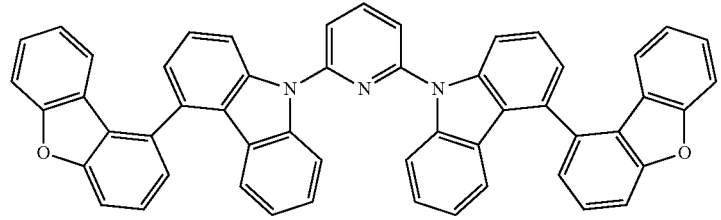
(48)
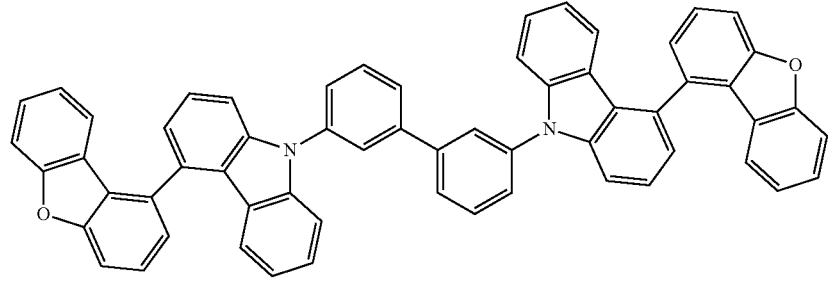
(49)
(50)
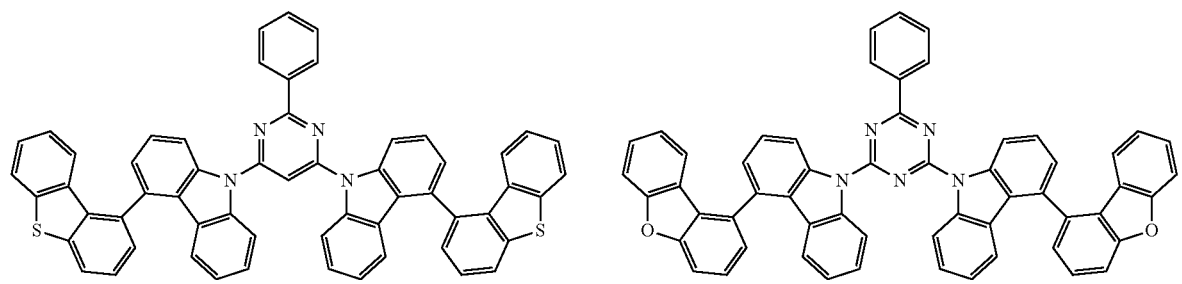
(51)
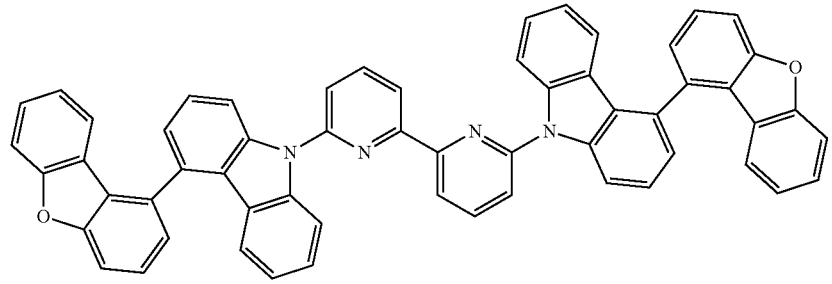

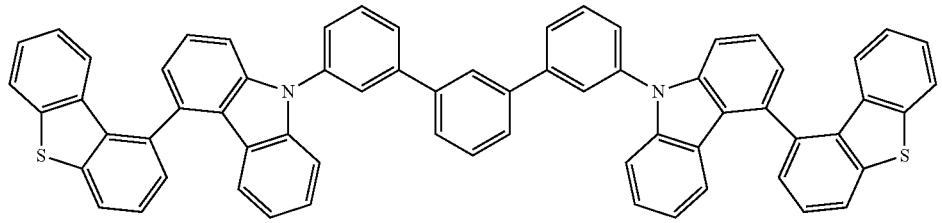
(52)
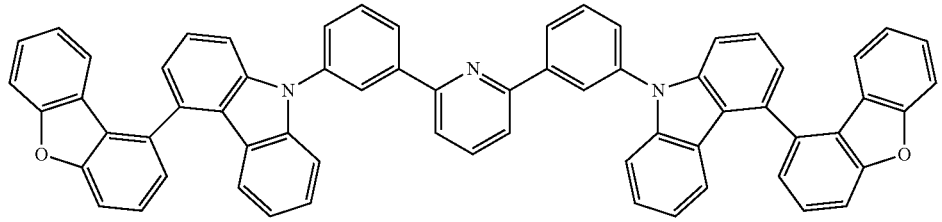
(53)
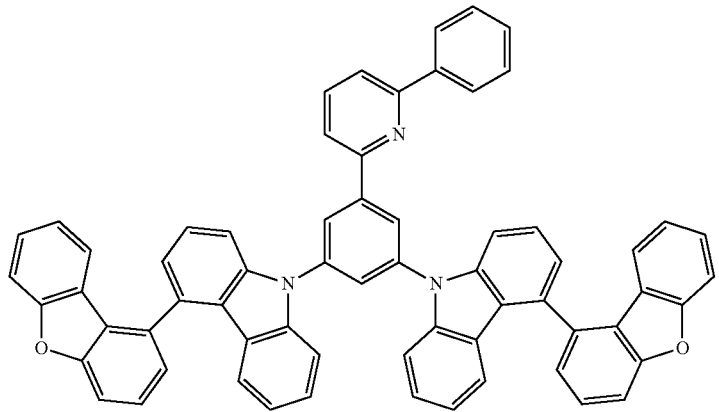
(54)
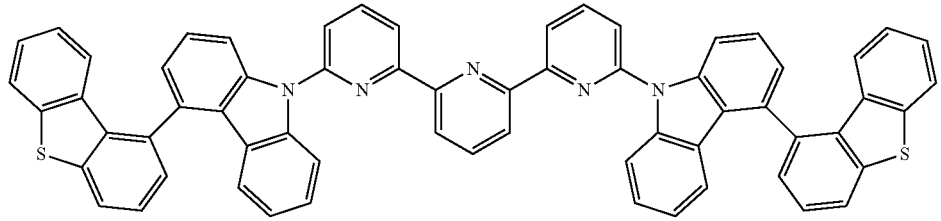
(55)
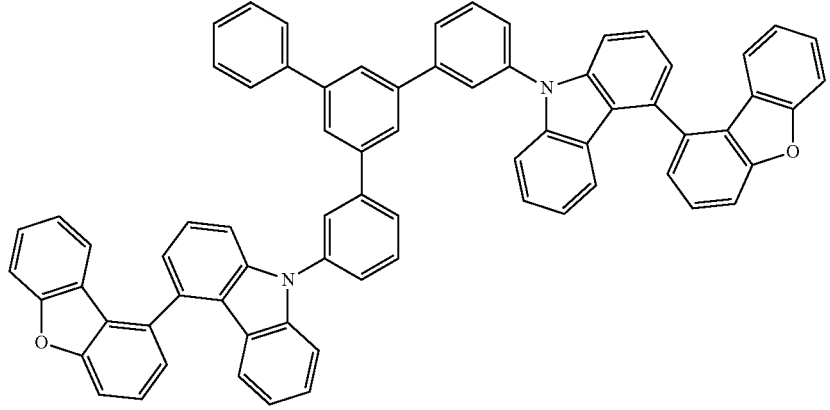
(56)

-continued
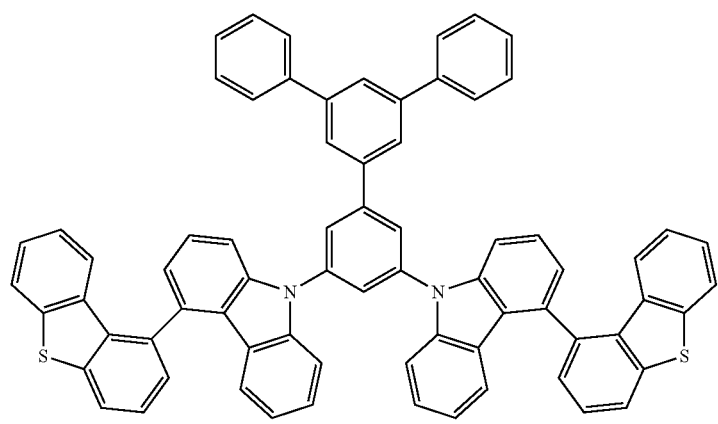
(57)
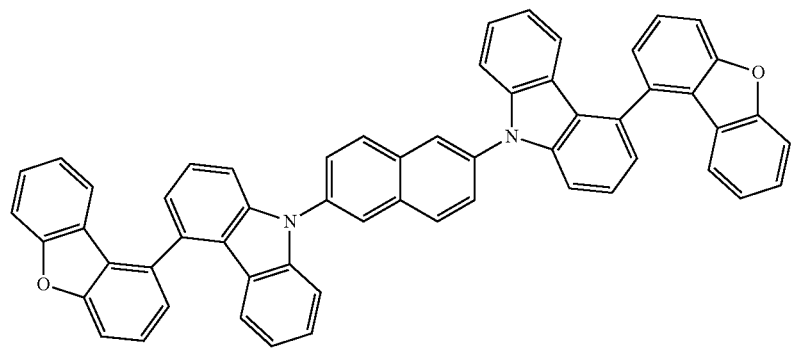
(58)
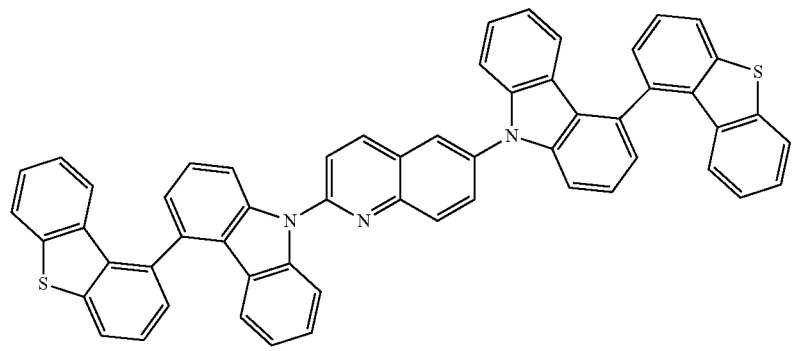
(59)
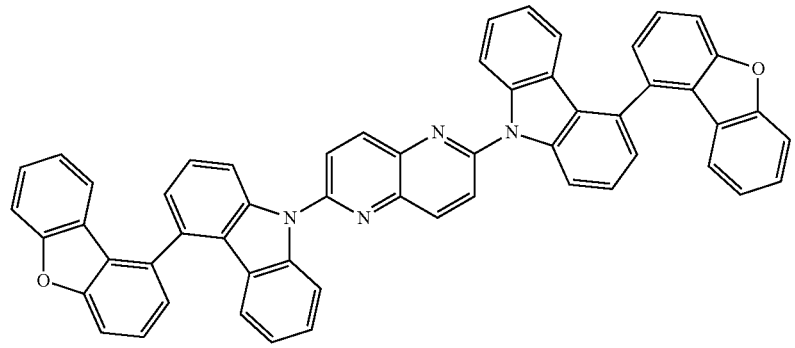
(60)

(84)
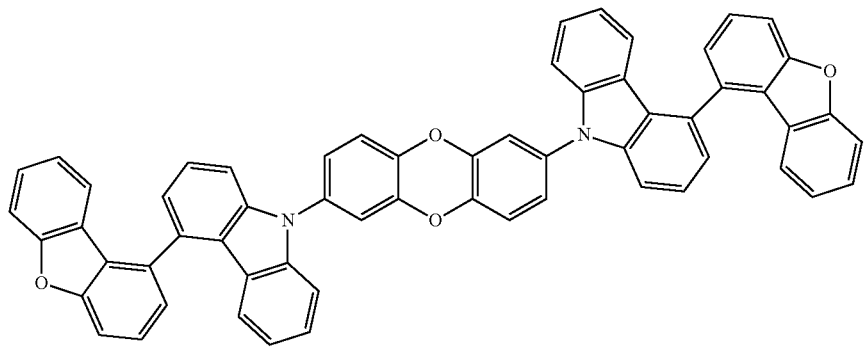
(85)
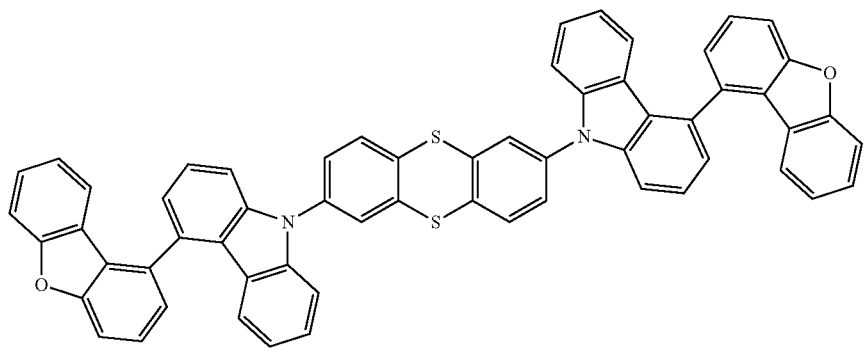
(86)
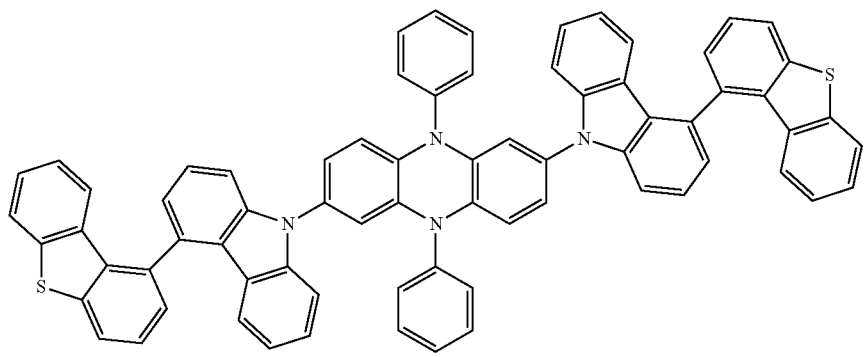
(87)
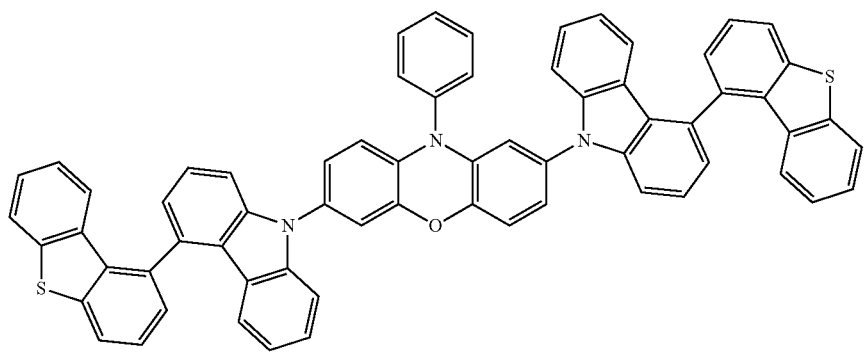

(88)
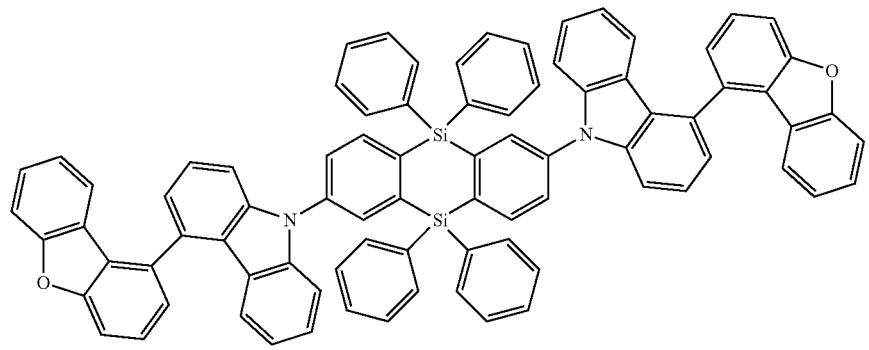
(89)
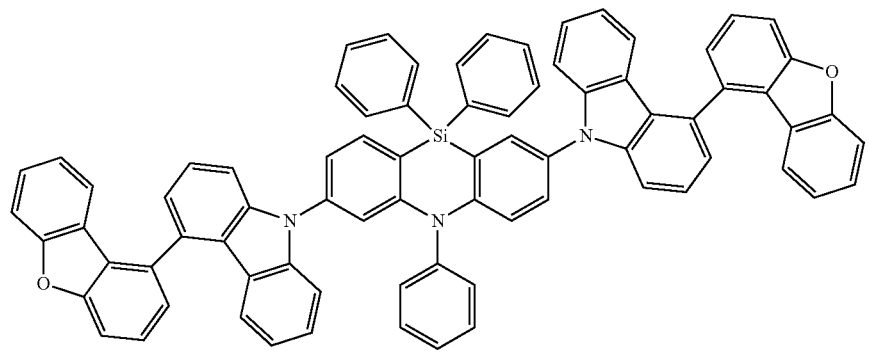
(90)
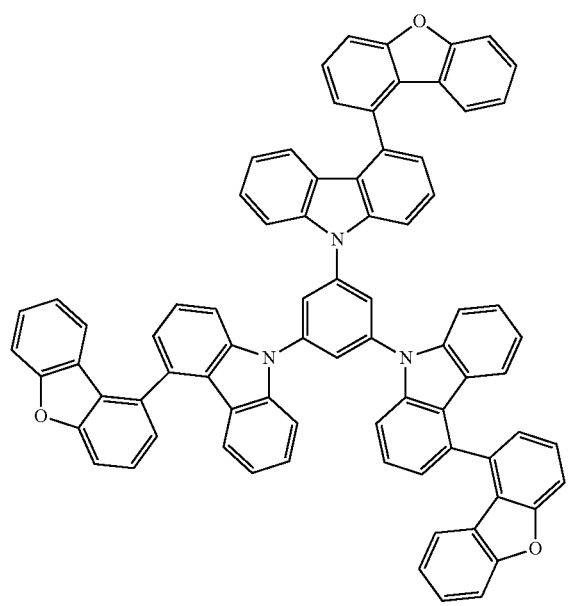
(91)
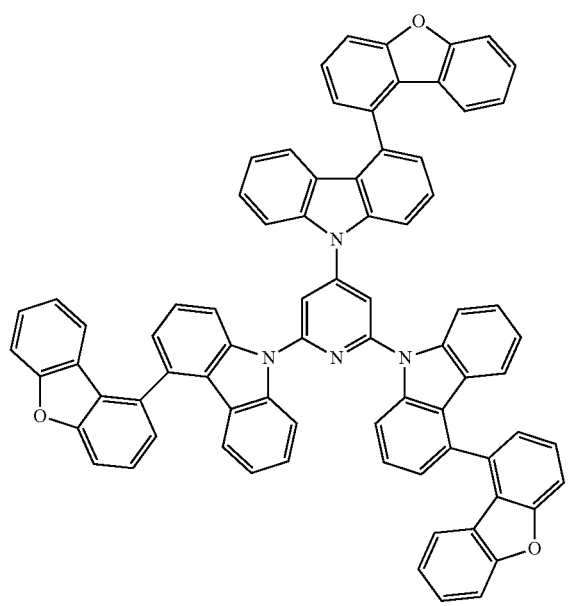

-continued
(92)
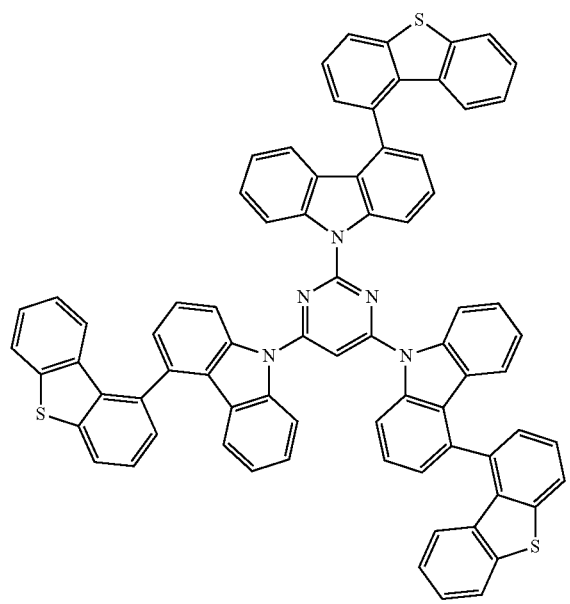
(93)
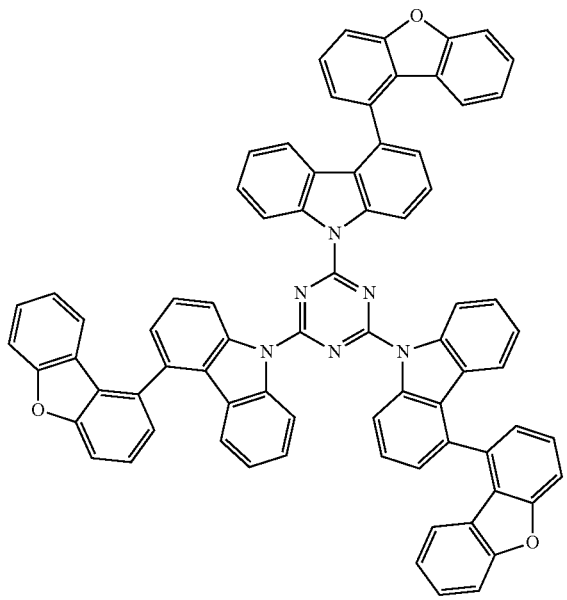
(94)
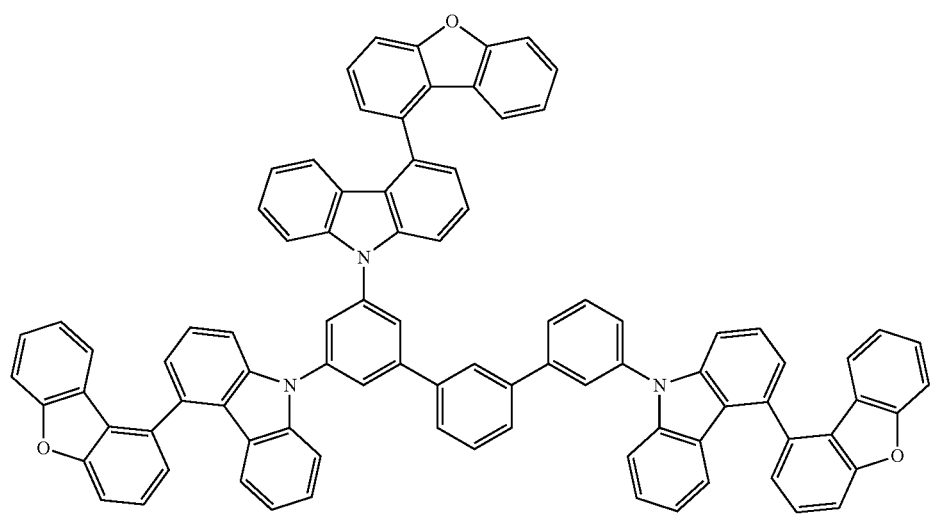
(95)
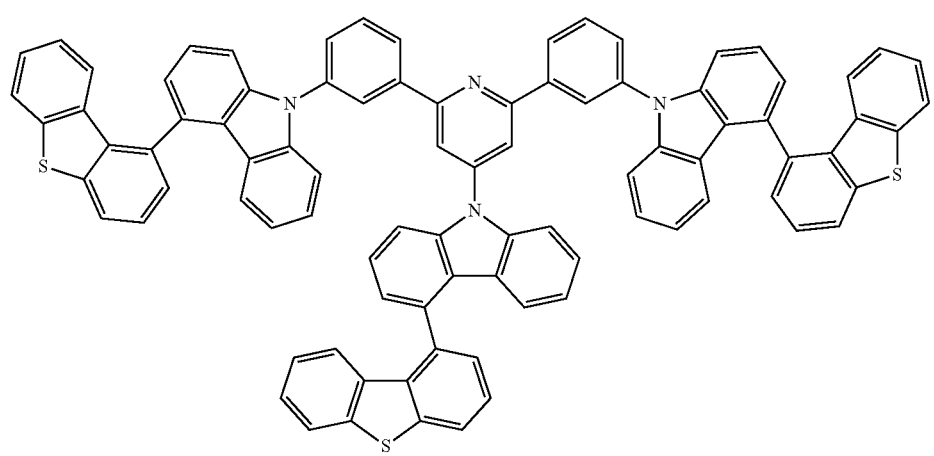

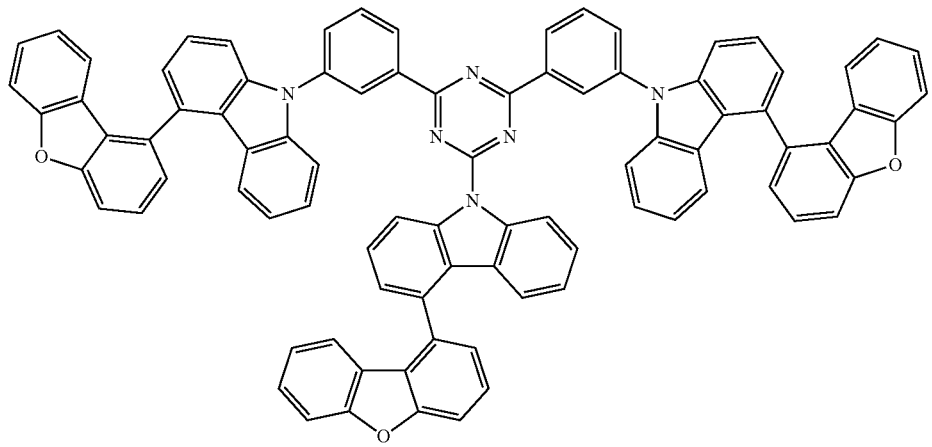

(96)

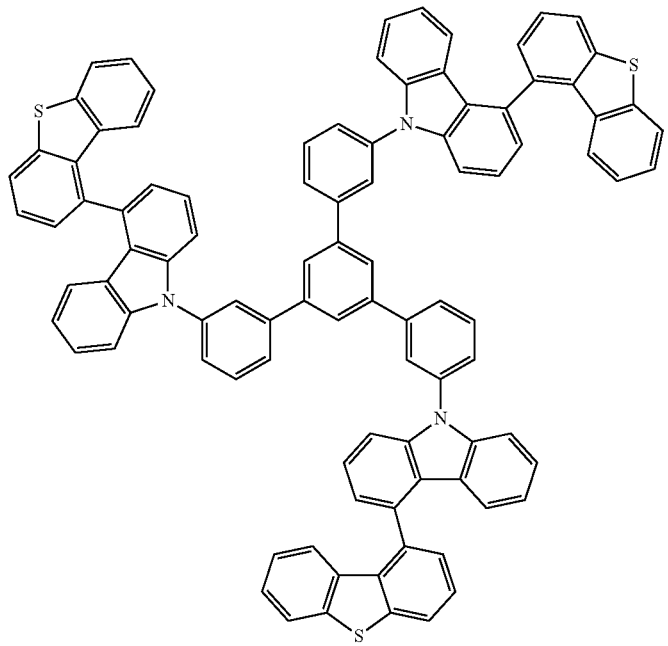

(97)

When the carbazole compound represented by the general formula (1) is incorporated into at least one of organic layers in an organic EL device formed by laminating an anode, a plurality of organic layers, and a cathode on a substrate, an excellent organic EL device is provided. The organic layers preferably include at least a light-emitting layer, and preferably further include a hole-transporting layer, an electron-transporting layer, a hole-blocking layer, an electron-blocking layer, or an exciton-blocking layer. A light-emitting layer, a hole-transporting layer, an electron-transporting layer, a hole-blocking layer, an electron-blocking layer, or an exciton-blocking layer is suitable as the organic layer into which the carbazole compound represented by the general formula (1) is incorporated. It is more preferred that the carbazole compound be incorporated as a host material in a light-emitting layer containing a phosphorescent light-emitting dopant.

The organic EL device of the present invention includes organic layers including at least one light-emitting layer between an anode and a cathode laminated on a substrate. In addition, at least one of the organic layers contains the carbazole compound represented by the general formula (1). The carbazole compound represented by the general formula (1) is advantageously contained in the light-emitting layer together with a phosphorescent light-emitting dopant.

Next, the structure of the organic EL device of the present invention is described with reference to the drawings. However, the structure of the organic EL device of the present invention is by no means limited to one illustrated in the drawings.

FIG. 1 is a sectional view illustrating an example of the structure of a general organic EL device. Reference numerals 1, 2, 3, 4, 5, 6, and 7 represent a substrate, an anode, a hole-injecting layer, a hole-transporting layer, a light-emitting layer, an electron-transporting layer, and a cathode, respectively. The organic EL device of the present invention may include an exciton-blocking layer adjacent to the light-emitting layer, or may include an electron-blocking layer between the light-emitting layer and the hole-injecting layer. The exciton-blocking layer may be inserted on any of the anode side and the cathode side of the light-emitting layer, and may also be inserted simultaneously on both sides. The organic EL device of the present invention includes the substrate, the anode, the light-emitting layer, and the cathode as its essential layers. The organic EL device of the present invention preferably includes a hole-injecting/transporting layer and an electron-injecting/transporting layer in addition to the essential layers, and more preferably includes a hole-blocking layer between the light-emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It should be noted that it is possible to adopt a reverse structure as compared to FIG. 1, that is, a structure formed by laminating the layers on the substrate 1 in the order of the cathode 7, the electron-transporting layer 6, the light-emitting layer 5, the hole-transporting layer 4, and the anode 2. In this case as well, a layer may be added or eliminated as required.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials such as CuI, indium tin oxide (ITO), $SnO_2$, and ZnO. Further, it may be possible to use a material such as IDIXO ($In_2O_3$—ZnO), which may be used for manufacturing an amorphous, transparent conductive film. In order to produce the anode, it may be possible to form any of those electrode substances into a thin film by using a method such as vapor deposition or sputtering and form a pattern having a desired shape thereon by photolithography. Alternatively, in the case of not requiring high pattern accuracy (about 100 μm or more), a pattern may be formed via a mask having a desired shape when any of the above-mentioned electrode substances is subjected to vapor deposition or sputtering. Alternatively, when a coatable substance such as an organic conductive compound is used, it is also possible to use a wet film-forming method such as a printing method or a coating method. When luminescence is extracted from the anode, the transmittance of the anode is desirably controlled to more than 10%. Further, the sheet resistance as the anode is preferably several hundred Ω/□ or less. Further, the thickness of the film is, depending on its material, selected from usually the range of from 10 to 1,000 nm, preferably the range of from 10 to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of electron-injecting property and durability against oxidation or the like. The cathode may be produced by forming any of those electrode substances into a thin film by using a method such as vapor deposition or sputtering. Further, the sheet resistance as the cathode is preferably several hundred Ω/□ or less, and the thickness of the film is selected from usually the range of from 10 nm to 5 μm, preferably the range of from 50 to 200 nm. It should be noted that, in order for luminescence produced to pass through, any one of the anode and cathode of the organic EL device is preferably transparent or semi-transparent, because the light emission luminance improves.

Further, after any of the above-mentioned metals is formed into a film having a thickness of from 1 to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and cathode have transparency.

—Light-Emitting Layer—

The light-emitting layer, which may be any one of a fluorescent light-emitting layer and a phosphorescent light-emitting layer, is preferably the phosphorescent light-emitting layer.

When the light-emitting layer is a fluorescent light-emitting layer, as a fluorescent light-emitting material, at least one kind of fluorescent light-emitting material may be used alone. However, it is preferred that the fluorescent light-emitting material be used as a fluorescent light-emitting dopant and a host material be contained.

The carbazole compound represented by the general formula (1) may be used as the fluorescent light-emitting material in the light-emitting layer. However, the fluorescent light-emitting material is known through many patent literatures and the like, and hence may be selected from those in the patent literatures and the like. Examples thereof include: a benzoxazole derivative, a benzothiazole derivative, a benzimidazole derivative, a styrylbenzene derivative, a polyphenyl derivative, a diphenylbutadiene derivative, a tetraphenylbutadiene derivative, a naphthalimide derivative, a coumarin derivative, a fused aromatic compound, a perinone derivative, an oxadiazole derivative, an oxazine derivative, an aldazine derivative, a pyrrolidine derivative, a cyclopentadiene derivative, a bisstyrylanthracene derivative, a quinacridone derivative, a pyrrolopyridine derivative, a thiadiazolopyridine derivative, a styrylamine derivative, a diketopyrrolopyrrole derivative, and an aromatic dimethylidyne compound; various metal complexes typified by a metal complex of an 8-quinolinol derivative and a metal complex, rare earth metal complex, or transition metal complex of a pyrromethene derivative; polymer compounds such as polythiophene, polyphenylene, and polyphenylene vinylene; and an organic silane derivative. Preferred examples thereof include a fused aromatic compound, a styryl compound, a diketopyrrolopyrrole compound, an oxazine compound, and a metal complex, transition metal complex, or lanthanoid complex of pyrromethene. More preferred examples thereof include naphthacene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthacene, hexacene, anthanthrene, naphtho[2,1-f]isoquinoline, α-naphthaphenanthridine, phenanthroxazole, quinolino[6,5-f]quinoline, and benzothiophanthrene. Each of those materials may have an alkyl group, an aryl group, an aromatic heterocyclic group, or a diarylamino group as a substituent.

When the fluorescent light-emitting material is used as the fluorescent light-emitting dopant and the host material is contained, the amount of the fluorescent light-emitting dopant to be incorporated into the light-emitting layer desirably falls within the range of from 0.01 to 20 wt %, preferably from 0.1 to 10 wt %.

In ordinary cases, the organic EL device is caused to emit light by producing a light-emitting substance in an excited state through the injection of charge into a light-emitting substance from each of both electrodes, i.e., the anode and the cathode. It is said that in the case of a charge injection-type organic EL device, 25% of produced excitons are excited to singlet excited states and the remaining 75% are excited to triplet excited states. As described in Advanced Materials 2009, 21, 4802-4806, a specific fluorescent light-emitting substance is known to express thermally activated delayed fluorescence via the following mechanism. After the transition of its energy into a triplet excited state through intersystem crossing or the like, the substance undergoes inverse intersystem crossing into a singlet excited state owing to triplet-triplet annihilation or the absorption of thermal energy, thereby radiating fluorescence. The organic EL device of the present invention can also express delayed fluorescence. In this case, the fluorescence can include both fluorescent emission and delayed fluorescent emission. It should be noted that light emission from the host material may constitute part of the light emission.

When the light-emitting layer is a delayed fluorescent light-emitting layer, a delayed fluorescent light-emitting material may be used alone in the light-emitting layer. However, it is preferred that the delayed fluorescent light-emitting material be used as a delayed fluorescent light-emitting dopant and the host material be mixed.

As the delayed fluorescent light-emitting material in the light emitting layer, the compound of the present invention may be used. However, the delayed fluorescent light-emitting material may be selected from known delayed fluorescent light-emitting materials. Examples thereof include, but not limited to, an indolocarbazole derivative disclosed in the non patent literature Appl. Phys. Lett. 98, 083302 (2011) and a carbazole derivative disclosed in Nature 492, 234 (2012).

Specific examples of the delayed fluorescent light-emitting material are shown below, but the delayed fluorescent light-emitting material is not limited to the following compounds.

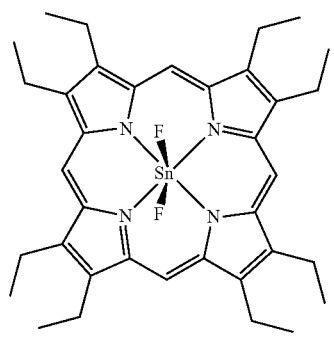

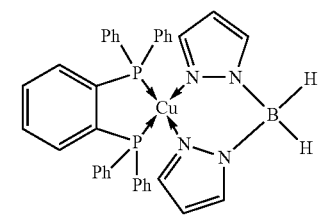

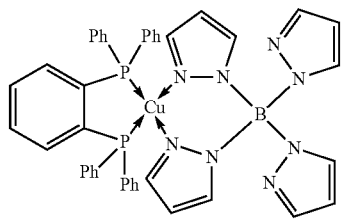

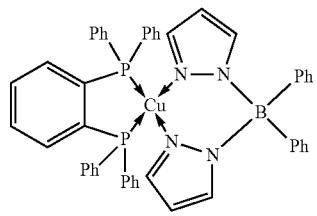

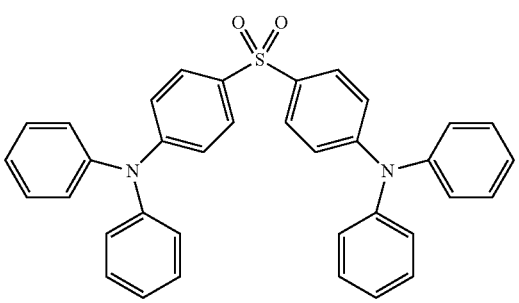

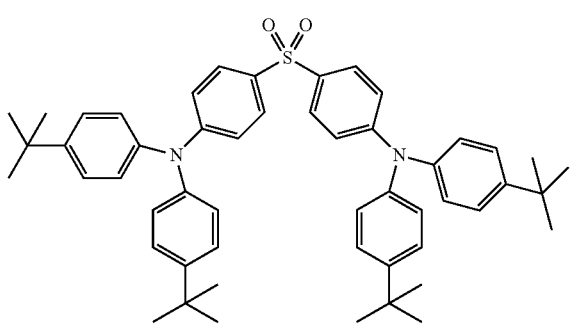

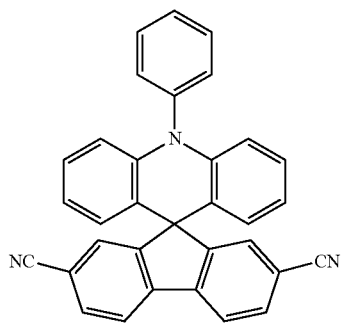

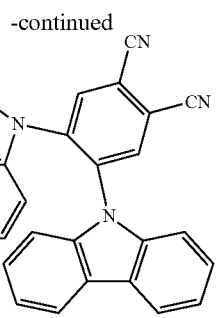

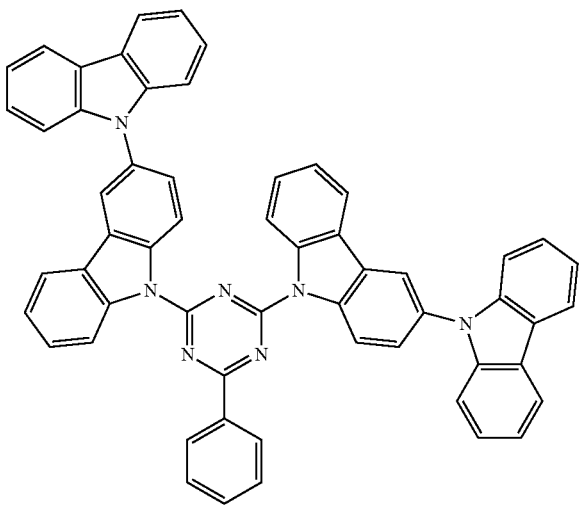

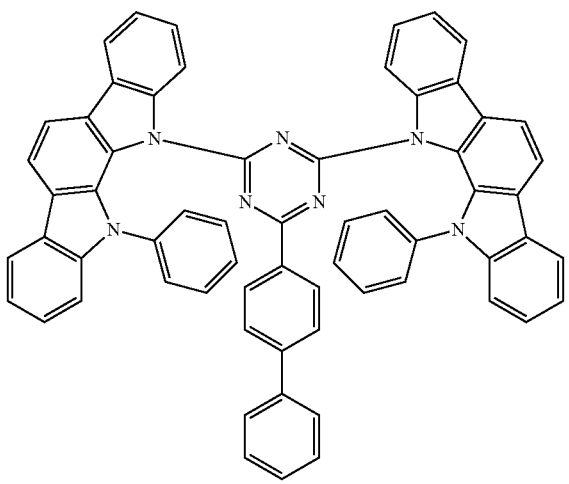

When the delayed fluorescent light-emitting material is used as a delayed fluorescent light-emitting dopant and the host material is contained, the content of the delayed fluorescent light-emitting dopant in the light-emitting layer desirably falls within the range of from 0.01 to 50 wt %, preferably from 0.1 to 20 wt %, more preferably from 0.01 to 10%.

The compound of the present invention may be used as the delayed fluorescent host material in the light-emitting layer. However, the delayed fluorescent host material may be selected from compounds other than the compound of the present invention. For example, the following compound may be used: a compound having a fused aryl ring such as naphthalene, anthracene, phenanthrene, pyrene, chrysene, naphthalene, triphenylene, perylene, fluoranthene, fluorene, or indene, or a derivative thereof; an aromatic amine derivative such as N,N'-dinaphthyl-N,N'-diphenyl-4,4'-diphenyl-1, 1'-diamine; a metal chelated oxinoid compound typified by tris(8-quinolinato)aluminum(III); a bisstyryl derivative such as a distyrylbenzene derivative; a tetraphenylbutadiene derivative; an indene derivative; a coumarin derivative; an oxadiazole derivative; a pyrrolopyridine derivative; a perinone derivative; a cyclopentadiene derivative; a pyrrolopyrrole derivative; a thiadiazolopyridine derivative; a dibenzofuran derivative; a carbazole derivative; an indolocarbazole derivative; a triazine derivative; or a polymer-based derivative such as a polyphenylene vinylene derivative, a poly-p-phenylene derivative, a polyfluorene derivative, a polyvinyl carbazole derivative, a polythiophene derivative, or an arylsilane derivative. However, the delayed fluorescent host material is not particularly limited thereto.

When the light-emitting layer is a phosphorescent light-emitting layer, the light-emitting layer contains a phosphorescent light-emitting dopant and a host material. It is recommended to use, as the phosphorescent light-emitting dopant, one containing an organic metal complex including at least one metal selected from ruthenium, rhodium, palladium, silver, rhenium, osmium, iridium, platinum, and gold. Specific examples thereof include, but not limited to, the compounds disclosed in the following patent literatures.

For example, WO 2009/073245 A1, WO 2009/046266 A1, WO 2007/095118 A1, WO 2008/156879 A1, WO 2008/140657 A1, US 2008/261076 A1, JP 2008-542203 A, WO 2008/054584 A1, JP 2008-505925 A, JP 2007-522126 A, JP 2004-506305 A, JP 2006-513278 A, JP 2006-50596 A, WO 2006/046980 A1, WO 2005/113704 A1, US 2005/260449 A1, US 2005/2260448 A1, US 2005/214576 A1, WO 2005/076380 A1, US 2005/119485 A1, WO 2004/045001 A1, WO 2004/045000 A1, WO 2006/100888 A1, WO 2007/004380 A1, WO 2007/023659 A1, WO 2008/035664 A1, JP 2003-272861 A, JP 2004-111193 A, JP 2004-319438 A, JP 2007-2080 A, JP 2007-9009 A, JP 2007-227948 A, JP 2008-91906 A, JP 2008-311607 A, JP 2009-19121 A, JP 2009-46601 A, JP 2009-114369 A, JP 2003-253128 A, JP 2003-253129 A, JP 2003-253145 A, JP 2005-38847 A, JP 2005-82598 A, JP 2005-139185 A, JP 2005-187473 A, JP 2005-220136 A, JP 2006-63080 A, JP 2006-104201 A, JP 2006-111623 A, JP 2006-213720 A, JP 2006-290891 A, JP 2006-298899 A, JP 2006-298900 A, WO 2007/018067 A1, WO 2007/058080 A1, WO 2007/058104 A1, JP 2006-131561 A, JP 2008-239565 A, JP 2008-266163 A, JP 2009-57367 A, JP 2002-117978 A, JP 2003-123982 A, JP 2003-133074 A, JP 2006-93542 A, JP 2006-131524 A, JP 2006-261623 A, JP 2006-303383 A, JP 2006-303394 A, JP 2006-310479 A, JP 2007-88105 A, JP 2007-258550 A, JP 2007-324309 A, JP 2008-270737 A, JP 2009-96800 A, JP 2009-161524 A, WO 2008/050733 A1, JP 2003-73387 A, JP 2004-59433 A, JP 2004-155709 A, JP 2006-104132 A, JP 2008-37848 A, JP 2008-133212 A, JP 2009-57304 A, JP 2009-286716 A, JP 2010-83852 A, JP 2009-532546 A, JP 2009-536681 A, and JP 2009-542026 A.

Preferred examples of the phosphorescent light-emitting dopant include complexes such as Ir(ppy)3, complexes such as Ir(bt)2(acac), and complexes such as PtOEt3, the complexes each having a noble metal element such as Ir as a central metal. Specific examples of those complexes are shown below, but the complexes are not limited to the compounds shown below.

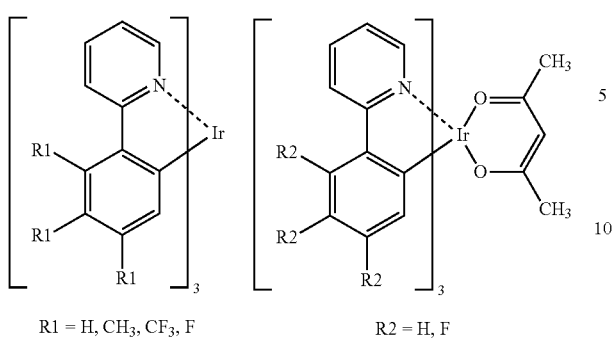
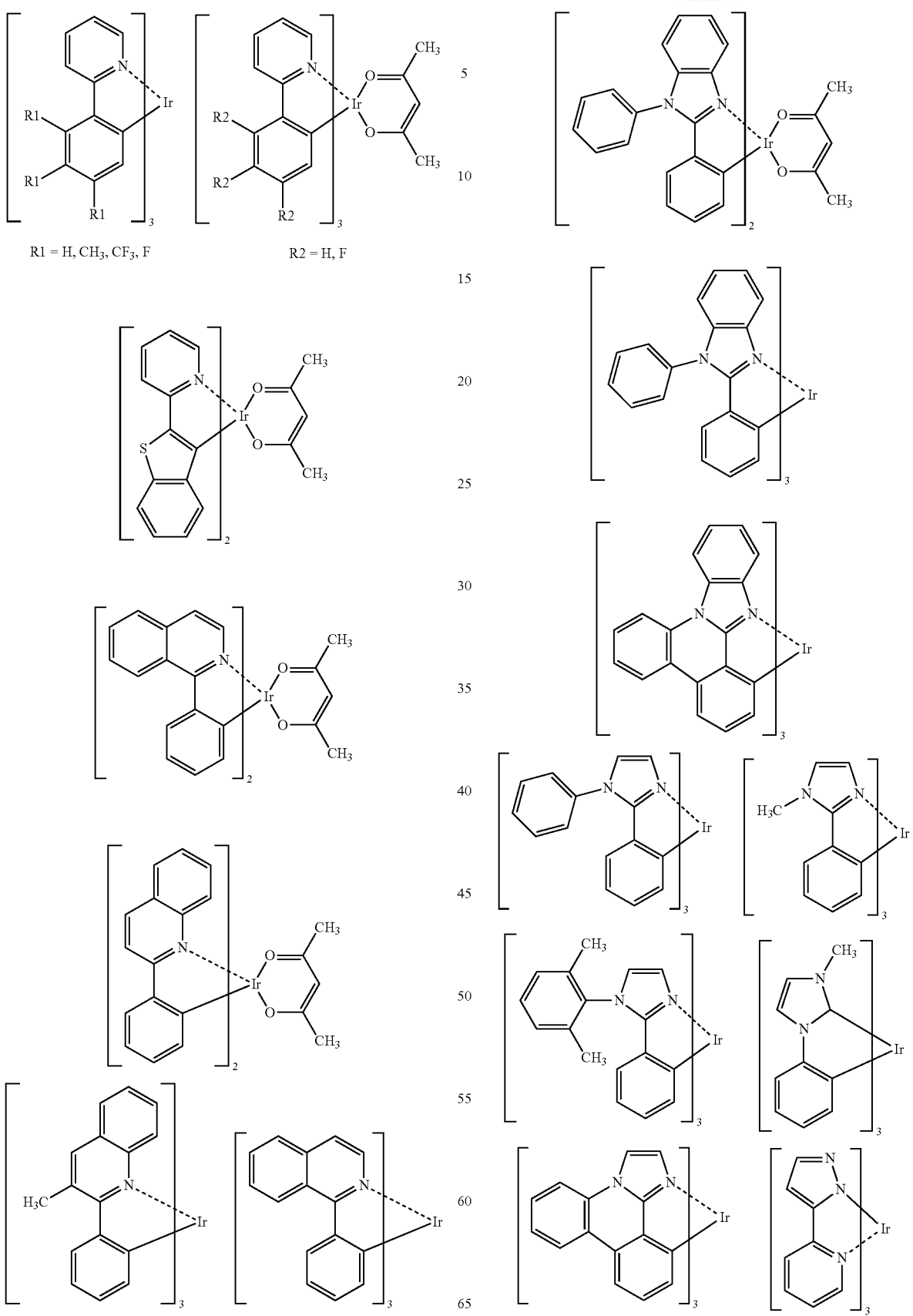

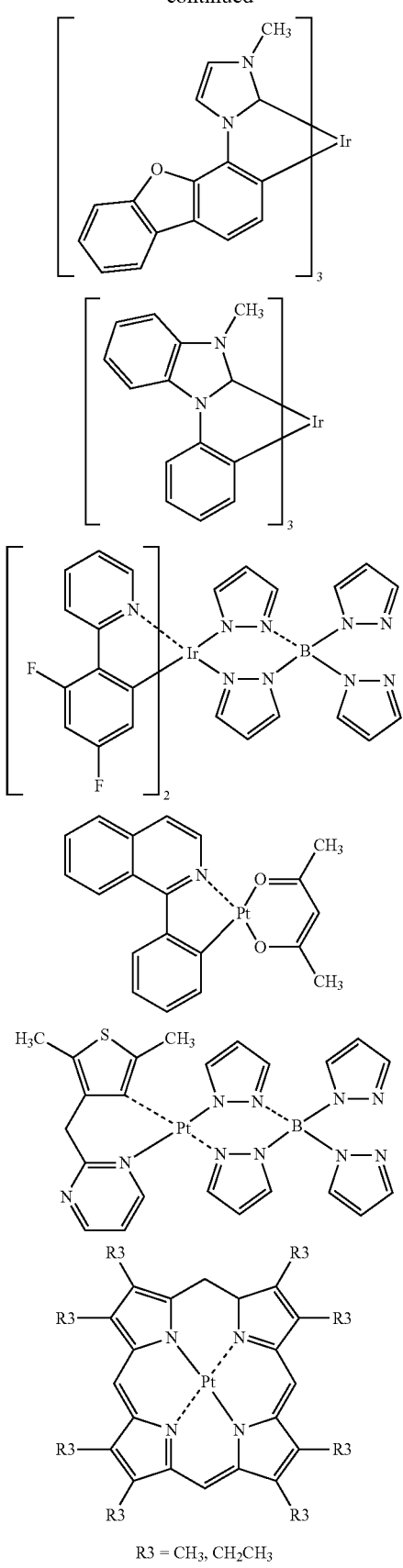

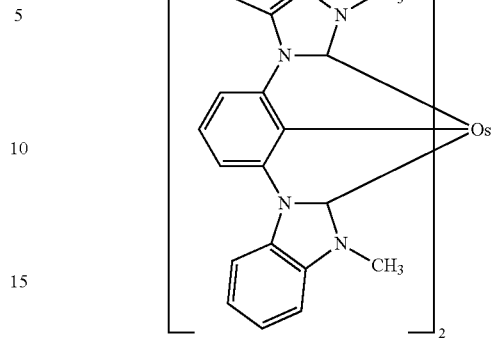

It is preferred that the content of the phosphorescent light-emitting dopant in the light-emitting layer fall within the range of from 0.1 to 50 wt %, more preferably from 1 to 30 wt %.

It is preferred to use, as the host material in the light-emitting layer, the carbazole compound represented by the general formula (1). However, when the carbazole compound is used in any of the organic layers other than the light-emitting layer, the material to be used in the light-emitting layer may be any other host material other than the carbazole compound represented by the general formula (1). In addition, the carbazole compound represented by the general formula (1) and the other host material may be used in combination. Further, a plurality of kinds of known host materials may be used in combination.

It is preferred to use, as a known host material that may be used, a compound that has a hole-transporting ability or an electron-transporting ability, is capable of preventing luminescence from having a longer wavelength, and has a high glass transition temperature.

Such other host material is known through many patent literatures and the like, and hence may be selected from those in the patent literatures and the like. Specific examples of the host material include, but not particularly limited to, an indole derivative, a carbazole derivative, an indolocarbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine derivative, an aromatic dimethylidene-based compound, a porphyrin-based compound, an anthraquinodimethane derivative, an anthrone derivative, a diphenylquinone derivative, a thiopyran dioxide derivative, a heterocyclic tetracarboxylic acid anhydride such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds such as a polysilane-based compound, a poly (N-vinylcarbazole) derivative, an aniline-based copolymer, a thiophene oligomer, a polythiophene derivative, a polyphenylene derivative, a polyphenylenevinylene derivative, and a polyfluorene derivative.

—Injecting Layer—

The injecting layer refers to a layer formed between an electrode and an organic layer for the purposes of lowering a driving voltage and improving light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be formed as required.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining a hole and an electron in the light-emitting layer by blocking holes while transporting electrons.

The carbazole compound represented by the general formula (1) is preferably used in the hole-blocking layer. However, when the carbazole compound is used in any other organic layer, a known hole-blocking material may be used. In addition, it is possible to use, as the material for the hole-blocking layer, any of materials for the electron-transporting layer to be described later as required.

—Electron-Blocking Layer—

The electron-blocking layer is formed of an electron-blocking material that has a remarkably small ability to transport electrons while having a function of transporting holes, and hence the electron-blocking layer is capable of improving the probability of recombining a hole and an electron in the light-emitting layer by blocking electrons while transporting holes.

The carbazole compound represented by the general formula (1) is preferably used as the material for the electron-blocking layer. However, when the carbazole compound is used in any other organic layer, a material for the hole-transporting layer to be described later may be used as required. The thickness of the electron-blocking layer is preferably from 3 to 100 nm, preferably from 5 to 30 nm.

—Exciton-Blocking Layer—

The exciton-blocking layer refers to a layer for blocking excitons produced by the recombination of a hole and an electron in the light-emitting layer from diffusing in charge-transporting layers. The insertion of this layer enables effective confinement of the excitons in the light-emitting layer, thereby being able to improve the luminous efficiency of the device. The exciton-blocking layer may be inserted on any of the anode side and cathode side of the adjacent light-emitting layer, and may also be inserted simultaneously on both sides.

The carbazole compound represented by the general formula (1) may be used as a material for the exciton-blocking layer. However, when the carbazole compound is used in any other organic layer, any material for an exciton-blocking layer selected from conventionally known compounds may be used. Examples of the known exciton-blocking material include 1,3-di(9-carbazolyl)benzene (mCP) and bis(2-methyl-8-quinolinolato)-4-phenylphenolatoaluminum(III) (BAlq).

—Hole-Transporting Layer—

The hole-transporting layer is formed of a hole-transporting material having a function of transporting holes, and a single hole-transporting layer or a plurality of hole-transporting layers may be formed.

The hole-transporting material has any one of hole-injecting property, hole-transporting property, and electron-blocking property, and any of an organic compound and an inorganic compound may be used. It is preferred to use the carbazole compound represented by the general formula (1) in the hole-transporting layer. However, when the carbazole compound is used in any other organic layer, any hole-transporting material selected from conventionally known compounds may be used. Examples of the known hole-transporting material that may be used include a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, a porphyrin compound, a polysilane-based compound, an aniline-based copolymer, and a conductive high-molecular oligomer, in particular, a thiophene oligomer. Of those, a porphyrin compound, an aromatic tertiary amine compound, or a styrylamine compound is preferably used, and an aromatic tertiary amine compound is more preferably used.

—Electron-Transporting Layer—

The electron-transporting layer is formed of an electron-transporting material having a function of transporting electrons, and a single electron-transporting layer or a plurality of electron-transporting layers may be formed.

An electron-transporting material (also serving as a hole-blocking material in some cases) only needs to have a function of transferring electrons injected from the cathode into the light-emitting layer. The carbazole compound represented by the general formula (1) is preferably used in the electron-transporting layer. However, when the carbazole compound is used in any other organic layer, any electron-transporting material selected from conventionally known compounds may be used. Examples thereof include a triazole derivative, an oxazole derivative, an imidazole derivative, a nitro-substituted fluorene derivative, an anthraquinodimethane derivative, an anthrone derivative, a diphenylquinone derivative, a thiopyran dioxide derivative, a carbodiimide derivative, a fluorenylidenemethane derivative, and an oxadiazole derivative. Further, it is also possible to use, as the electron-transporting material, a thiadiazole derivative prepared by substituting an oxygen atom on an oxadiazole ring with a sulfur atom in the oxadiazole derivative and a quinoxaline derivative that has a quinoxaline ring known as an electron withdrawing group. Further, it is also possible to use a polymer material in which any of those materials is introduced in a polymer chain or is used as a polymer main chain.

EXAMPLES

The present invention is hereinafter described in more detail byway of Examples. Needless to say, the present invention is not limited to Examples below and may be carried out in various forms as long as the various forms do not deviate from the gist of the present invention.

The synthesis route described below was used to synthesize the carbazole compound represented by the general formula (1) used in the present invention. It should be noted

Synthesis Example 1

Synthesis of Compound (23)

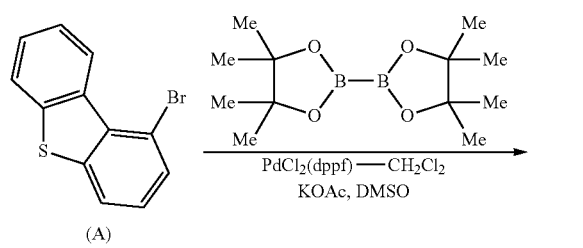

(A)

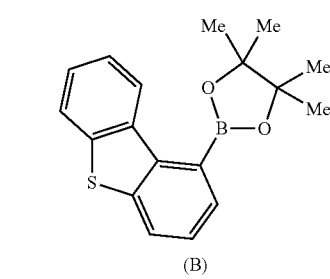

(B)

Under a nitrogen atmosphere, while 16.02 g (0.061 mol) of 1-bromodibenzo[b,d]thiophene (A), 23.20 g (0.091 mol) of bis(pinacolato)diboron, 17.93 g (0.18 mol) of potassium acetate, and 400 ml of dimethyl sulfoxide were stirred at room temperature, 2.49 g (0.0031 mol) of a [1,1'-bis(diphenylphosphino)ferrocene]dichloropalladium(II) dichloromethane complex were added to the mixture. After that, the mixture was stirred for 4 hr while being heated at 80° C. After the reaction solution had been cooled to room temperature, 2,400 ml of distilled water were added to the solution and the solution was extracted with ethyl acetate (3×600 ml). An organic layer was washed with 400 ml of distilled water and dried with anhydrous magnesium sulfate, and then the solvent was removed by distillation under reduced pressure. The resultant residue was purified by silica gel column chromatography to provide 12.09 g (0.039 mol, 64% yield) of boronic acid pinacol ester (B).

The APCI-TOFMS of the compound showed an [M]+ ion peak at an m/z of 310.

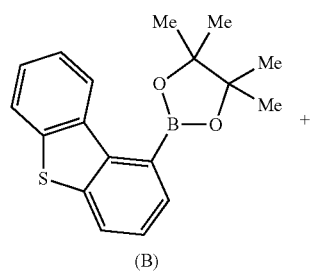

(B)

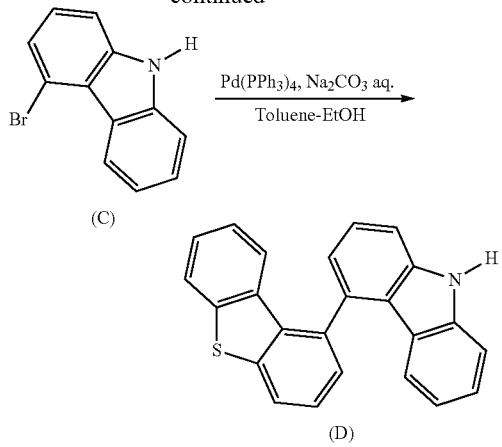

Under a nitrogen atmosphere, while 4.19 g (0.017 mol) of 4-bromocarbazole (C), 6.87 g (0.022 mol) of the boronic acid pinacol ester (B), 36 ml of an aqueous solution (2.0 mol/l) of sodium carbonate, 43 ml of ethanol, and 128 ml of toluene were stirred at room temperature, 0.393 g (0.00034 mol) of tetrakis(triphenylphosphine)palladium(0) was added to the mixture. After that, the mixture was stirred for 19.5 hr while being heated to reflux at 70° C. After the reaction solution had been cooled to room temperature, 40 ml of distilled water were added to the solution. The solution was concentrated and then extracted with dichloromethane (3×150 ml). An organic layer was dried with anhydrous magnesium sulfate and then the solvent was removed by distillation under reduced pressure. The resultant residue was purified by silica gel column chromatography to provide 5.55 g (0.016 mol, 93% yield) of 4-(1-dibenzo[b,d]thienyl)carbazole (D) as a white solid.

The APCI-TOFMS of the compound showed an [M]+ ion peak at an m/z of 349.

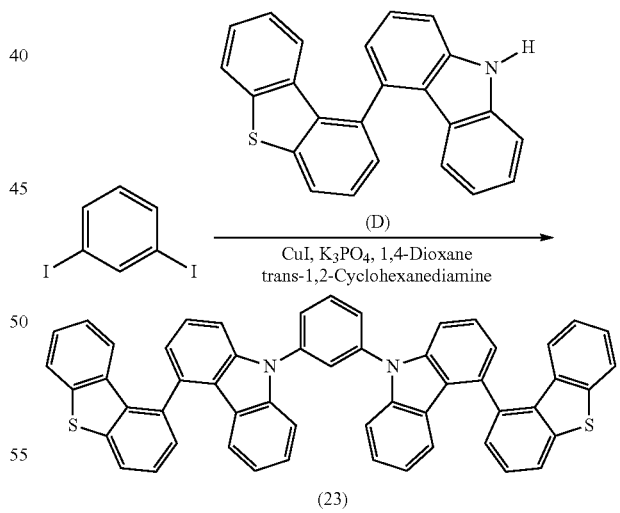

(23)

Under a nitrogen atmosphere, while 2.33 g (0.0071 mol) of 1,3-diiodobenzene, 5.43 g (0.016 mol) of 4-(1-dibenzo[b,d]thienyl)carbazole (D), 0.142 g (0.00071 mol) of copper (I) iodide, 6.00 g (0.028 mol) of tripotassium phosphate, and 140 ml of anhydrous 1,4-dioxane were stirred at room temperature, 0.85 ml (0.0071 mol) of trans-1,2-cyclohexanediamine was added to the mixture. After that, the mixture was stirred for 16 hr while being heated to reflux at 100° C. After the reaction solution had been cooled to room temperature, an inorganic salt was separated by filtration and the solvent was removed by distillation under reduced pressure. The resultant residue was purified by silica gel column chromatography. The purified product was further purified by reslurrying under heat to provide 5.36 g (0.0069 mol, 98% yield) of the compound (23) as a white solid.

Figure 2:
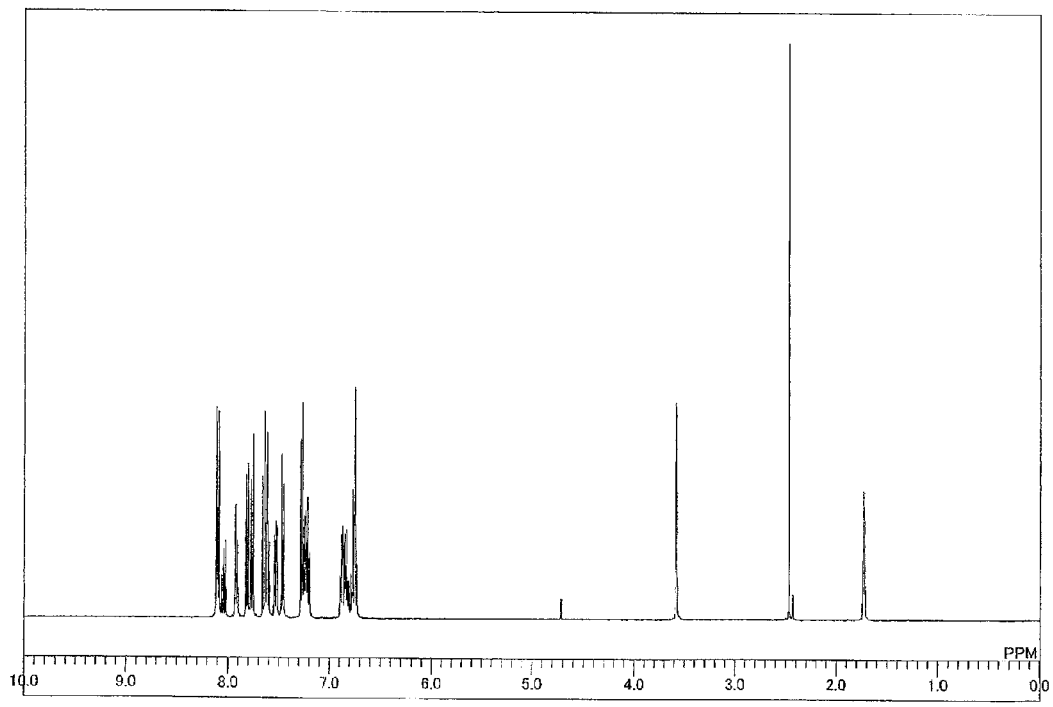
FIG. 2 is a $^1$H-NMR chart of a carbazole compound (23).

FIG. 2 shows the results of $^1$H-NMR measurement (400 MHz, THF-d8) of the compound (23).

The APCI-TOFMS of the compound showed an [M+H]$^+$ ion peak at an m/z of 773.

Example 1

Each thin film was laminated by a vacuum deposition method at a degree of vacuum of $2.0 \times 10^{-5}$ Pa on a glass substrate on which an anode formed of indium tin oxide (ITO) having a thickness of 110 nm had been formed. First, copper phthalocyanine (CuPC) was formed into a layer having a thickness of 25 nm to serve as a hole-injecting layer on the ITO. Next, 4,4'-bis[N-(1-naphthyl)-N-phenylamino]biphenyl (NPD) was formed into a layer having a thickness of 90 nm to serve as a hole-transporting layer. Next, the compound (23) as a host material for a light-emitting layer and bis[2-(4,6-difluorophenyl)pyridinato-N,C2'](picolinato)iridium (FIrpic) as a blue phosphorescent light-emitting material, were co-deposited from different deposition sources onto the hole-transporting layer to form a light-emitting layer having a thickness of 30 nm. At this time, the concentration of FIrpic was 10 wt %. Next, tris(8-hydroxyquinoline)aluminum (Alq3) was formed into a layer having a thickness of 30 nm to serve as an electron-transporting layer. Further, lithium fluoride (LiF) was formed into a layer having a thickness of 1 nm to serve as an electron-injecting layer on the electron-transporting layer. Finally, aluminum (Al) was formed into a layer having a thickness of 70 nm to serve as an electrode on the electron-injecting layer. Thus, an organic EL device was produced.

An external power source was connected to the resultant organic EL device to apply a DC voltage. As a result, it was confirmed that the organic EL device had such light-emitting characteristics as shown in Table 1. A luminance, voltage, and luminous efficiency in Table 1 show values at 2.5 mA/cm$^2$. It should be noted that it was found that the local maximum wavelength of the emission spectrum of the device was 475 nm and hence light emission from FIrpic was obtained.

Examples 2 and 3

Organic EL devices were each produced in the same manner as in Example 1 except that the compound (48) or (53) was used instead of the compound (23) as the host material for the light-emitting layer in Example 1. It was identified that the local maximum wavelength of the emission spectrum of each of the devices was 475 nm and hence light emission from FIrpic was obtained. Table 1 shows the light-emitting characteristics of each of the devices.

Comparative Example 1

An Organic EL device was produced in the same manner as in Example 1 except that 1,3-di(9-carbazolyl)benzene (mCF) was used as the host material for the light-emitting layer in Example 1. It was identified that the local maximum wavelength of the emission spectrum of the device was 475 nm and hence light emission from FIrpic was obtained. Table 1 shows its light-emitting characteristics.

Comparative Examples 2 and 3

Organic EL devices were each produced in the same manner as in Example 1 except that a compound (H1) or (H2) was used as the host material for the light-emitting layer in Example 1. It was identified that the local maximum wavelength of the emission spectrum of each of the devices was 475 nm and hence light emission from FIrpic was obtained. Table 1 shows the light-emitting characteristics of each of the devices.

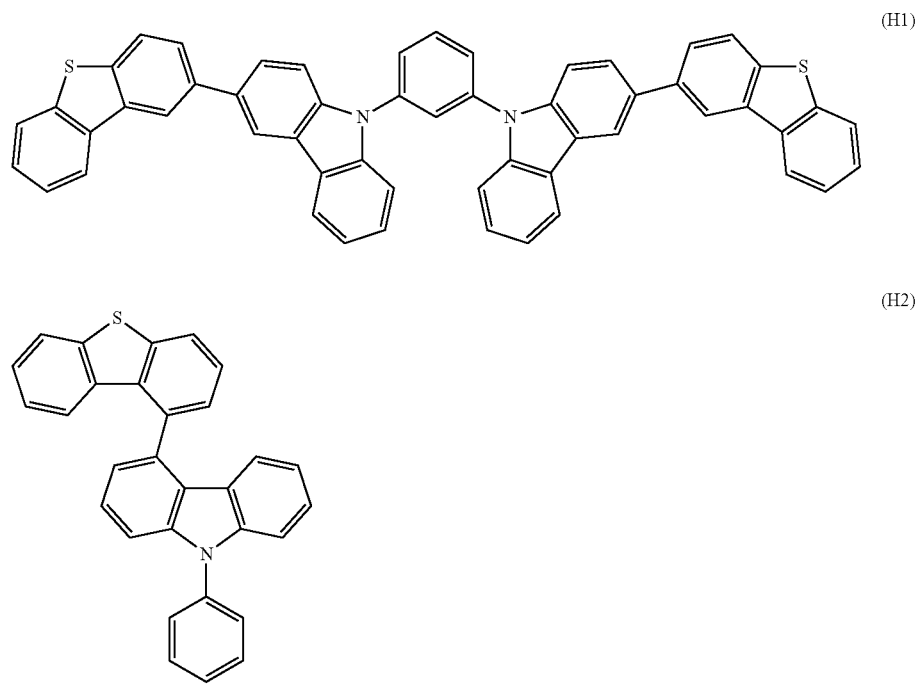

TABLE 1

|  | Host compound | Luminance (cd/m²) | Voltage (V) | Visual luminous efficiency (lm/W) |
|---|---|---|---|---|
| Example 1 | (23) | 196 | 8.2 | 3.0 |
| Example 2 | (48) | 224 | 8.6 | 3.3 |
| Example 3 | (53) | 181 | 8.6 | 2.6 |
| Comparative Example 1 | mCP | 140 | 8.7 | 2.0 |
| Comparative Example 2 | (H1) | 151 | 8.9 | 2.1 |
| Comparative Example 3 | (H2) | 143 | 8.8 | 2.0 |

Example 4

Each thin film was laminated by a vacuum deposition method at a degree of vacuum of $2.0 \times 10^{-5}$ Pa on a glass substrate on which an anode formed of indium tin oxide (ITO) having a thickness of 110 nm had been formed. First, copper phthalocyanine (CuPC) was formed into a layer having a thickness of 25 nm to serve as a hole-injecting layer on the ITO. Next, 4,4'-bis[N-(1-naphthyl)N-phenylamino] biphenyl (NPD) was formed into a layer having a thickness of 40 nm to serve as a hole-transporting layer. Next, the compound (23) as a host material for a light-emitting layer and tris(2-phenylpyridine)iridium (Ir(ppy)3) as a green phosphorescent light-emitting material were co-deposited from different deposition sources onto the hole-transporting layer to form a light-emitting layer having a thickness of 40 nm. At this time, the concentration of Ir(ppy)3 was 10 wt %. Next, tris(8-hydroxyquinoline)aluminum (Alq3) was formed into a layer having a thickness of 20 nm to serve as an electron-transporting layer. Further, lithium fluoride (LiF) was formed into a layer having a thickness of 1 nm to serve as an electron-injecting layer on the electron-transporting layer. Finally, aluminum (Al) was formed into a layer having a thickness of 70 nm to serve as an electrode on the electron-injecting layer. Thus, an organic EL device was produced.

An external power source was connected to the resultant organic EL device to apply a DC voltage. As a result, it was confirmed that the organic EL device had such light-emitting characteristics as shown in Table 2. A luminance, voltage, and luminous efficiency in Table 2 show values at 20 mA/cm². It should be noted that it was found that the local maximum wavelength of the emission spectrum of the device was 530 nm and hence light emission from Ir(ppy)3 was obtained.

Examples 5 to 8

Organic EL devices were each produced in the same manner as in Example 4 except that the compound (48), (50), (51), or (53) was used instead of the compound (23) as the host material for the light-emitting layer in Example 4. It was identified that the local maximum wavelength of the emission spectrum of each of the devices was 530 nm and hence light emission from Ir(ppy)3 was obtained. Table 2 shows the light-emitting characteristics of each of the devices.

Comparative Example 4

Organic EL devices were each produced in the same manner as in Example 4 except that 4,4'-di(9-carbazolyl) biphenyl (CBP) was used as the host material for the light-emitting layer in Example 4. It was identified that the local maximum wavelength of the emission spectrum of the device was 530 nm and hence light emission from Ir(ppy)3 was obtained. Table 2 shows its light-emitting characteristics.

Comparative Examples 5 and 6

Organic EL devices were each produced in the same manner as in Example 4 except that the compound (H1) or (H2) was used as the host material for the light-emitting layer in Example 4. It was identified that the local maximum wavelength of the emission spectrum of each of the devices was 530 nm and hence light emission from Ir(ppy)3 was obtained. Table 2 shows the light-emitting characteristics of each of the devices.

TABLE 2

|  | Host compound | Luminance (cd/m²) | Voltage (V) | Visual luminous efficiency (lm/W) |
|---|---|---|---|---|
| Example 4 | (23) | 2,050 | 8.6 | 3.7 |
| Example 5 | (48) | 2,350 | 8.5 | 4.3 |
| Example 6 | (50) | 2,330 | 8.1 | 4.5 |
| Example 7 | (51) | 2,520 | 8.1 | 4.9 |
| Example 8 | (53) | 1,940 | 8.9 | 3.4 |
| Comparative Example 4 | CBP | 1,120 | 8.7 | 2.0 |
| Comparative Example 5 | (H1) | 1,270 | 9.0 | 2.2 |
| Comparative Example 6 | (H2) | 1,180 | 9.0 | 2.1 |

The invention claimed is:

1. An organic electroluminescent device, having a structure in which an anode, an organic layer, and a cathode are laminated on a substrate, wherein at least one layer selected from the group consisting of a light-emitting, layer, a hole-transporting layer, an electron-transporting layer, a hole-blocking layer, an electron-blocking layer, and an exciton-blocking layer contains a carbazole compound represented by the general formula (1):

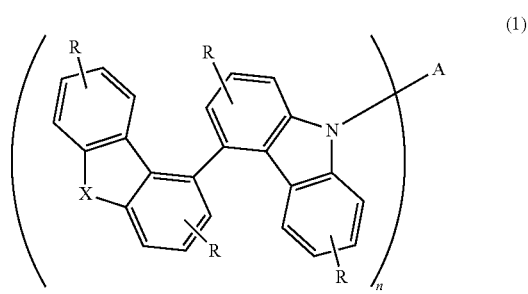

wherein:
A represents an n-valent aromatic hydrocarbon group having 6 to 30 carbon atoms, an n-valent aromatic heterocyclic group having 3 to 30 carbon atoms, or an n-valent aromatic group in which two to six of the aromatic hydrocarbon groups and the aromatic heterocyclic groups are linked to each other;
n represents an integer of 2 or 3;
when the aromatic hydrocarbon group or the aromatic heterocyclic group has substituents, the substituents each independently comprise an alkyl group having 1 to 10 carbon atoms, a cycloalkyl group having 3 to 10 carbon atoms, an alkoxy group having 1 to 10 carbon atoms, —OAr, —N(Ar)$_2$, or —Si(Ar)$_3$;

R's each independently represent hydrogen, an alkyl group having 1 to 10 carbon atoms, a cycloalkyl group having 3 to 10 carbon atoms, an alkoxy group having 1 to 10 carbon atoms, —OAr, —N(Ar)$_2$, —Si(Ar)$_3$, an aromatic hydrocarbon group having 6 to 10 carbon atoms, an aromatic heterocyclic group having 3 to 10 carbon atoms, or an aromatic group in which two to three of the aromatic hydrocarbon groups and the aromatic heterocyclic groups are linked to each other;

Ar's each independently represent an aromatic hydrocarbon group having 6 to 10 carbon atoms, an aromatic heterocyclic group having 3 to 10 carbon atoms, or an aromatic group in which two to three of the aromatic hydrocarbon groups and the aromatic heterocyclic groups are linked to each other; and X's each independently represent oxygen or sulfur.

2. An organic electroluminescent device according to claim 1, wherein R's each represent hydrogen.

3. An organic electroluminescent device according to claim 1, wherein A represents an n-valent aromatic group represented by any one of the following formulae (2) to (5):

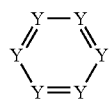
(2)

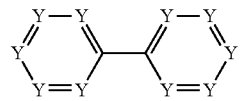
(3)

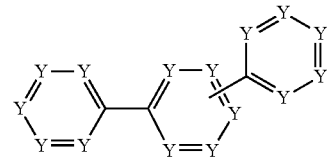
(4)

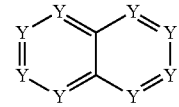
(5)

in the formulae (2) to (5):

Y's each independently represent C, C(R), or nitrogen, and n Y's each represent C, provided that n+1 Y's in the formula (4) each represent C; and n and R each have the same meaning as that in the general formula (1).

4. An organic electroluminescent device according to claim 1, wherein the layer containing the carbazole compound represented by the general formula (1) is a light-emitting layer containing a phosphorescent light-emitting dopant.

* * * * *